United States Patent
Gerecht et al.

(10) Patent No.: US 10,143,776 B2
(45) Date of Patent: *Dec. 4, 2018

(54) FUNCTIONAL VASCULARIZATION WITH BIOCOMPATIBLE POLYSACCHARIDE-BASED HYDROGELS

(75) Inventors: Sharon Gerecht, Baltimore, MD (US); Guoming Sun, Baltimore, MD (US); Yu-I Shen, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 619 days.

This patent is subject to a terminal disclaimer.

(21) Appl. No.: 13/807,502

(22) PCT Filed: Jun. 30, 2011

(86) PCT No.: PCT/US2011/042671
§ 371 (c)(1),
(2), (4) Date: Dec. 28, 2012

(87) PCT Pub. No.: WO2012/003370
PCT Pub. Date: Jan. 5, 2012

(65) Prior Publication Data
US 2013/0102531 A1    Apr. 25, 2013

Related U.S. Application Data

(60) Provisional application No. 61/360,178, filed on Jun. 30, 2010.

(51) Int. Cl.
| | | |
|---|---|---|
| *A61K 38/19* | (2006.01) | |
| *A61L 27/26* | (2006.01) | |
| *A61K 31/721* | (2006.01) | |
| *A61L 27/52* | (2006.01) | |
| *A61K 38/30* | (2006.01) | |
| *A61K 38/18* | (2006.01) | |
| *A61L 27/54* | (2006.01) | |
| *A61K 9/00* | (2006.01) | |
| *A61K 45/06* | (2006.01) | |

(52) U.S. Cl.
CPC ............ *A61L 27/26* (2013.01); *A61K 9/0024* (2013.01); *A61K 31/721* (2013.01); *A61K 38/1866* (2013.01); *A61K 38/1891* (2013.01); *A61K 38/195* (2013.01); *A61K 38/30* (2013.01); *A61K 45/06* (2013.01); *A61L 27/52* (2013.01); *A61L 27/54* (2013.01); *A61L 2300/414* (2013.01); *A61L 2300/45* (2013.01); *A61L 2430/32* (2013.01)

(58) Field of Classification Search
None
See application file for complete search history.

(56) References Cited

U.S. PATENT DOCUMENTS

| | | |
|---|---|---|
| 5,334,640 A | 8/1994 | Desai et al. |
| 5,591,709 A | 1/1997 | Lindenbaum |
| 6,476,204 B1 | 11/2002 | Kim et al. |
| 6,602,952 B1 | 8/2003 | Bentley et al. |
| 7,799,767 B2 | 9/2010 | Lamberti et al. |
| 2002/0081729 A1 | 6/2002 | Peters et al. |
| 2004/0151752 A1 | 8/2004 | Won et al. |
| 2006/0024357 A1 | 2/2006 | Carpenter et al. |
| 2008/0020015 A1 | 1/2008 | Carpenter et al. |
| 2009/0022777 A1 | 1/2009 | Mathiowitz et al. |
| 2009/0130755 A1 | 5/2009 | Detamore et al. |
| 2009/0280182 A1 | 11/2009 | Beck et al. |
| 2011/0275565 A1 | 11/2011 | Gerecht et al. |
| 2012/0225814 A1 | 9/2012 | Hanjaya-Putra et al. |

FOREIGN PATENT DOCUMENTS

| | | | |
|---|---|---|---|
| WO | WO-2003/072155 A1 | 9/2003 | |
| WO | WO-2006/060779 A2 | 6/2006 | |
| WO | WO-2008/098019 A2 | 8/2008 | |
| WO | WO-2010/078036 A2 | 7/2010 | |
| WO | WO 2010078036 A2 * | 7/2010 | ............... A61K 9/06 |
| WO | WO-2011/060095 A2 | 5/2011 | |
| WO | WO-2012003370 A2 | 1/2012 | |
| WO | WO-2012/158312 A2 | 11/2012 | |

OTHER PUBLICATIONS

Hao et al. Angiogenic effects of sequential release of VEGF-A165 and PDGF-BB with alginate hydrogels after myocardial infarction. Cardiovascular Research. 2007; 75 (1):178-185.*
Sun et al. Functional groups affect physical and biological properties of dextran-based hydrogels. Journal of Biomaterials Research Part A, published online Sep. 14, 2009; pp. 1080-1090.*
Chiu et al. Scaffolds with covalently immobilized VEGF and Angiopoietin-1 for vascularization of engineered tissues. Biomaterials, published online Oct. 2, 2009; 31: 226-241.*
Sun et al. Effects of Precursor and Cross-linking Parameters on the Properties of Dextran-Allyl Isocyanate-Ethylamine/Poly(ethylene glycol diacrylate) Biodegradable Hydrogels and Their Release of Ovalbumin. Journal of Biomaterials Science. 2009; 2003-2022).*

(Continued)

*Primary Examiner* — Vanessa L. Ford
*Assistant Examiner* — Sandra E Dillahunt
(74) *Attorney, Agent, or Firm* — Venable LLP; Keith G. Haddaway; Miguel A. Lopez

(57) ABSTRACT

Slow vascularization of functional blood limits the transplantation of tissue constructs and the recovery of ischemic and wounded tissues. Blood vessel ingrowth into polysaccharide-based hydrogel scaffolds remains a challenge. A synergistic effect of multiple angiogenic GFs was established; the co-encapsulation of VEGF plus other growth factors induced more and larger blood vessels than any individual GF, while the combination of all GFs dramatically increased the size and number of newly formed functional vessels. Rapid, efficient, and functional neovascularization may be achieved.

15 Claims, 15 Drawing Sheets

(56) References Cited

OTHER PUBLICATIONS

Chiu et al. Chiu et al. Scaffolds with covalently immobilized VEGF and Angiopoietin-1 for vascularization of engineered tissues. Biomaterials, published online Oct. 2, 2009; 31: 226-241.Biomaterials, published online Oct. 2, 2009; 31: 226-241.*
Sun et al. Effects of precursor and cross-linking parameters on the properties of dextran allyl isocyanate ethylamine/PEGDA biodegradable hydrogels and their release of ovalbumin. Journal of Biomaterials Science. 2009; 2003-2022.*
Chiu et al. Scaffolds with covalently immobilized VEGF and angiopoietin-1 for vascaularization of engineered tissues. Biomaterials, published online Oct. 2, 2009; 31: 226-241 (Year: 2009).*
Sun et al. Journal of Biomaterials Research Part A, published online Sep. 14, 2009; pp. 1080-1090). (Year: 2009).*
Office Action issued in U.S. Appl. No. 13/140,324 dated Oct. 29, 2013.
Office Action issued in U.S. Appl. No. 13/508,821 dated Nov. 22, 2013.
Extended European Search Report issued in European Patent Application No. 11801440.6 dated Jan. 30, 2014.
Chiu et al., "Scaffolds with covalently immobilized VEGF and Angiopoietin-1 for vascularization of engineered tissues", Biomaterials, vol. 31, p. 226-241, Oct. 2, 2009.
Hasan et al., "Adaptation to oxygen deprivation in cultures of human pluripotent stem cells, endothelial progenitor cells, and umbilical vein endothelial cells", Am J Physiol Cell Physiol., vol. 298, pp. C1527-C1537 Feb. 24, 2010.
International Search Report issued in Application No. PCT/EP2011/042671, dated Feb. 17, 2012.
Written Opinion issued in Application No. PCT/EP2011/042671, dated Feb. 17, 2012.
Adams et al., Trends in Cardiovascular Medicine, vol. 17, No. 7,pp. 246-251, 2007.
Asahara et al., Circulation, vol. 92, No. 9, pp. 365-371, 1995.
Azzam et al., *Macromol. Symp.*, 2003, vol. 195, p. 247.
Banfi et al., Curr Atheroscler Rep vol. 7, No. 3, pp. 227-234, 2005.
Bos et al., Biomaterials vol. 26, No. 18, pp. 3901-3909, 2005.
Cao et al., Biomaterials, vol. 27, No. 14, pp. 2854-2864, 2006.
Chen et al., Arterioscler Thromb Vasc Biol vol. 28, No. 9, pp. 1606-1613, 2008.
Chung et al., *Int. J. Biol. Macromol.*, 2003, vol. 32, p. 17.
de Jong et al., *Macromolecules*, 2000, vol. 33, p. 3680.
Delafontaine et al., Arterioscler Thromb Vasc Biol, vol. 24, No. 3, pp. 435-444, 2004.
Dvir et al., Proc Natl Acad Sci U S A vol. 106, No. 35, pp. 14990-14995, 2009.
Edman, et al., *I. J. Pharm. Sci.* 1980, vol. 69, pp. 838-842.
Elia et al., Biomaterials, vol. 31, No. 17, pp. 4630-4638, 2010.
Fan et al., FASEB J, vol. 22, No. 10, pp. 3571-3580 2008.
Ferreira et al., Biomaterials vol. 28, No. 17, pp. 2706-2717, 2007.
Fleissner et al., Mol Med vol. 14, No. 5-6, pp. 235-237, 2008.
Gong et al., Adv Mater, vol. 15, No. 14, pp. 1155-1158, 2003.
Greenwald et al., *Adv. Drug Deli. Rev.*, 2003, vol. 55, p. 217.
Guiducci et al., vol. 47, suppl. 5, pp. v18-v20, 2008.
Hanjaya-Putra et al., Biotechnol Prog, vol. 25, No. 1, pp. 2-9, 2009.
Heinze et al., In *Polysaccharides Ii*, Springer-Verlag Berlin: Berlin, 2006; p. 199.
Hennick et al. Adv. Drug Deli. Rev., vol. 54, No. 1, pp. 13-36, 2002.
Hern et al., *J. Biomed. Mater. Res.*,, 1998, vol. 39. p. 266.
Hosack et al., Biomaterials vol. 29, No. 15, 2336-47, 2008.
Ito et al., *Biomaterials*, 2007, vol. 28, pp. 3418-3426.
Keskar et al., J Tissue Eng Regen Med, vol. 3, No. 6, pp. 486-490, 2009.
Kim et al., *J. Biomed. Mater. Res.*, 2000, vol. 53, pp. 258-266.
Kim et al., *Arch. Pharma. Res.*, 2001, vol. 24, p. 69.
Kim et al., *J. Biomater. Appl.*, 2000, vol. 15, p. 23.
Kopecek, J. *Nature* 2002, vol. 417, pp. 388-391.
Koumenis et al., *Int. J. Pharma.*, 2000, vol. 198, p. 83.
Kraehenbuehl et al., Biomaterials vol. 30, No. 26, pp. 4318-4324, 2009.

Langer, Science, vol. 249, No. 4976, pp. 1527-1533, 1990.
Lee et al., Nature vol. 408, No. 6815, pp. 998-1000, 2000.
Maia et al., "Synthesis and characterization of new injectable and degradable dextran-based hydrogels," *Polymer*, 2005, vol. 46, pp. 9604-9614.
Massia et al., *Biomaterials*, 2000, vol. 21, pp. 2253.
Mikos et al., Biotechnol Bioeng, vol. 42, No. 6, pp. 716-723, 1993.
Murphy et al., Biomaterials, vol. 21, No. 24, pp. 2521-2527, 2000.
Peattie et al., vol. 25, No. 14, pp. 2789-2798, 2004.
Peppas et al., *Europ. J. Pharma. Biopharma.*, 2000, vol. 50, p. 27.
Perets et al., J Biomed Mater Res Part A, vol. 65A, No. 4, pp. 489-497, 2003.
Petit et al., Trends Immunol vol. 28, No. 7, pp. 299-307, 2007.
Phelps et al., Proc Natl Acad Sci U S A, vol. 107, No. 8, pp. 3323-3328, 2010.
Pike et al., Biomaterials, vol. 27, No. 30, pp. 5242-5251, 2006.
Prior et al., J Appl Physiol vol. 97, No. 3, pp. 1119-1128, 2004.
Rafii et al., Nat Med, vol. 9, No. 6, pp. 702-712, 2003.
Ravi et al., Regenerative Medicine vol. 5, No. 1, 107-20, 2010.
Richardson et al., Nat Biotech vol. 19, No. 11, pp. 1029-1034, 2001.
Riley et al., Biomaterials vol. 27, No. 35, pp. 5935-5943, 2006.
Sales et al., Trends Biotechnol, vol. 23, No. 9, pp. 461-467, 2005.
Sheridan et al., J Controlled Release, vol. 64, No. 1-3, pp. 91-102, 2000.
Srivastava et al.. Nature vol. 441, No. 7079, pp. 1097-1099, 2006.
Sun et al., Carbohydr Polym, vol. 65, No. 3, pp. 273-287, 2006.
Sun et al., J Biomed Mater Res Part A, vol. 93A, No. 3, pp. 1080-1090, 2010.
Sun et al., Biomaterials, vol. 32, p. 95, 2011.
Sun et al., J Biomater Sci-Polym Ed vol. 20, No. 14, pp. 2003-2022, 2009.
Sun et al., Regenerative Medicine, vol. 3, No. 3, 435-47, 2009.
Urbich et al., Circ Res, vol. 95, No. 4, pp. 343-353, 2004.
Van Tomme et al. *Expert Rev. Med. Dev.* 2007, vol. 4, pp. 147-164.
Van Tomme et al., *Biomaterials*, 2006, vol. 27, p. 4141.
vanDijkWolthuis et al., *Macromolecules*, 1995, vol. 28, pp. 6317-6322.
vanDijkWolthuis et al., *Macromolecules*, 1997, vol. 30, pp. 4639-4645.
vanDijkWolthuis et al., *Polymer*, 1997, vol. 38, pp. 6235-6242.
Wang et al., *J. Membr. Sci.*, 2002, vol. 195, p. 103.
Won et al., *Carbohydr. Polym.*, 1998, vol. 36, p. 327.
Won et al., in: *Biomaterials & Engineering Handbook*, D. L. Wise (Ed.), p. 356. Marcel Dekker, New York, NY (2000).
Yang et al., Tissue Engineering vol. 7, No. 6, 679-89, 2001.
Zhang et al., *Biomaterials*, 2002, vol. 23, p. 2641-2648.
Zhang et al., *J. Biomater. Appl.*, 2002, vol. 16, p. 305.
Zhang et al., *J. Polym. Sci. Polym. Chem.*, 1999, vol. 37, pp. 4554-4569.
Zhang et al., *J. Polym. Sci. Polym. Chem.*, 2000, vol. 38, pp. 2392-2404.
Aicher et al., "Mobilizing Endothelial Progenitor Cells," *Hypertension*, vol. 45, pp. 321-325, 2005.
Asahara et al., "Bone Marrow Origin of Endothelial Progenitor Cells responsible for Postnatal Vasculogenesis in Physiological and Pathological Neovascularization," *Circ. Res.*, vol. 85, pp. 221-228, 1999.
Asahara et al., "Isolation of Putative Progenitor Endothelial Cells for Angiogenesis," *Science*, vol. 275, pp. 964-967, 1997.
Au et al., "Bone marrow-derived mesenchymal stem cells facilitate engineering of long-lasting functional vasculature," *Blood*, vol. 111, No. 9, pp. 4551-4558, 2008.
Au et al., "Differential in vivo potential of endothelial progenitor cells from human umbilical cord blood and adult peripheral blood to form functional long-lasting vessels," *Blood*, vol. 111, pp. 1302-1305, 2008.
Bayless et al., "RGD-Dependent Vacuolation and Lumen Formation Observed during Endothelial Cell Morphogenesis in Three-Dimensional Fibrin Matrices Involves the $\alpha_r\beta_3$ and $\alpha_5\beta_1$ Integrins," *Am. J. Pathol.*, vol. 156, No. 5, pp. 1673-1683, 2000.
Bayless et al., "The Cdc42 and Rac1 GTPases are required for capillary lumen formation in three-dimensional extracellular matrices," *J. Cell Sci.*, vol. 115, pp. 1123-1136, 2002.

(56) References Cited

OTHER PUBLICATIONS

Bettinger et al., "Enhancement in IN Vitro Capillary Tube Formation by Substrate Nanotopography," *Adv. Mater.*, vol. 20, pp. 99-103, 2008.
Boudou et al., "An extended relationship for the characterization of Young's modulus and Poisson's ratio of tunable polyacrylamide gels," *Biorheology*, vol. 43, pp. 721-728, 2006.
Burdick et al., "Controlled Degradation and Mechanical Behavior of Photopolymerized Hyaluronic Acid Networks," *Biomacromolecules*, vol. 6, No. 1, pp. 386-391, 2005.
Chen et al., "Geometric Control of Cell Life and Death," *Science*, vol. 276, pp. 1425-1428, 1997.
Chun et al., "MT1-MMP-dependent neovessel formation within the confines of the three-dimensional extracellular matrix," *J. Cell. Biol.*, vol. 167, pp. 757-767, 2004.
Collen et al., "Membrane-type matrix metalloproteinase-mediated angiogenesis in a fibrin-collagen matrix," *Blood*, vol. 101, pp. 1810-1817, 2003.
Critser et al., "Collagen matrix physical properties modulate endothelial colony forming cell-derived vessels in vivo." *Microvascular Research*, vol. 80, pp. 23-30, 2010.
Davis et al., "An $\alpha 2\beta 1$ Integrin-Dependent Pinocytic Mechanism Involving Intracellular Vacuole Formation and Coalescence Regulates Capillary Lumen and Tube Formation in Three-Dimensional Collagen Matric," *Exp. Cell. Res.*, vol. 224, pp. 39-51, 1996.
Davis et al., "Endothelial Extracellular Matrix: Biosynthesis, Remodeling, and Functions During Vascular Morphogenesis and Neovessel Stabilization," *Circ Res.*, vol. 97, pp. 1093-1107, 2005.
Davis et al., "Extracellular matrix mediates a molecular balance between vascular morphogenesis and regression," *Current Opinion in Hematology*, vol. 15, No. 3, pp. 197-203, 2008.
Davis et al., "Regulation of Endothelial Cell Morphogenesis by Integrins, Mechanical Forces, and Matrix Guidance Pathways," *Exp. Cell Res.*, vol. 216, pp. 113-123, 1995.
Davis, "The development of the vasculature and its extracellular matrix: a gradual process defined by sequential cellular and matrix remodeling events," *Am. J. Physiol. Heart Circ. Physiol.*, vol. 299, pp. H245-H247, 2010.
Deroanne et al., "In vitro tubulogenesis of endothelial cells by relaxation of the coupling extracellular matrix-cytoskeleton," *Cardiovasc. Res.*, vol. 49, pp. 647-658, 2001.
Discher et al., "Tissue Cells Feel and Respond to the Stiffness of Their Substrate," *Science*, vol. 310, pp. 1139-1143, 2005.
Ehrbar et al., "Cell-Demanded Liberation of $VEGF_{121}$ From Fibrin Implants Induces Local and Controlled Blood Vessel Growth," *Circ Res*, vol. 94, No. 8, pp. 1124-1132, 2004.
Engler et al., "Matrix Elasticity Directs Stem Cell Lineage Specification," *Cell*, vol. 126, pp. 677-689, 2006.
Ferreira et al., "Vascular Progenitor Cells Isolated From Human Embryonic Stem Cells Give Rise to Endothelial and Smooth Muscle-Like Cells and Form Vascular Networks In Vivo," *Circ. Res.*, vol. 101, pp. 286-294, 2007.
Folkman et al., "Angiogenesis in vitro," *Nature*, vol. 288, pp. 551-556, 1980.
Galis et al., "Increased Expression of Matrix Metalloproteinases and Matrix Degrading Activity in Vulnerable Regions of Human Atherosclerotic Plaques," *J. Clin. Invest.*, vol. 94, pp. 2493-2503, 1994.
Galvez et al., "Membrane Type 1-Matrix Metalloproteinase Is Activated during Migration of Human Endothelial Cells and Modulates Endothelial Motility and Matrix Remodeling," *J. Biol. Chem.*, vol. 276, pp. 37491-37500, 2001.
Genasetti et al., "Hyaluronan and Human Endothelial Cell Behavior," *Connect. Tissue Res.*, vol. 49, No. 3, pp. 120-123, 2008.
Gerecht et al., "Hyaluronic acid hydrogel for controlled self-renewal and differentiation of human embryonic stem cells," *Proc. Natl. Acad. Sci. U. S. A.*, vol. 104, pp. 11298-11303, 2007.
Gerecht et al., "The effect of actin disrupting agents on contact guidance of human embryonic stem cells," *Biomaterials*, vol. 28, pp. 4068-4077, 2007.

Ghosh et al., "Cell adaptation to a physiologically relevant ECM mimic with different viscoelastic properties," *Biomaterials*, vol. 28, pp. 671-679, 2007.
Gobin et al., "Cell migration through defined, synthetic extracellular matrix analogues," *FASEB J.*: 01-0759fje, pp. 1-16, 2002.
Guo et al., "Synthesis and characterization of novel biodegradable unsaturated poly(exter amide)/poly(ethylene glycol) diacrylate hydrogels," *Journal of Polymer Science Part A—Polymer Chemistry*, vol. 43, No. 17, pp. 3932-3944, 2005.
Guo et al., "Biodegradation of unsaturated poly(ester-amide)s and their hydrogels," *Biomaterials*, vol. 28, pp. 3284-3294, 2007.
Haas, "Endothelial cell regulation of matrix metalloproteinases," *Can. J. Physiol. Pharmacol.*, vol. 83, pp. 1-7, 2005.
Han et al., "TNF-$\alpha$ stimulates activation of pro-MMP2 in human skin through NF-$\kappa$B mediated induction of MT1-MMP," *Journal of Cell Science*, vol. 114, pp. 131-139, 2001.
Hanjaya-Putra et al., "Vascular Engineering Using Human Embryonic Stem Cells," *Biotechnology Progress*, vol. 25, Iss. 1, pp. 2-6, 2009.
Hill et al., "Circulating Endothelial Progenitor Cells, Vascular Function and cardiovascular Risk," *New England J. Med.*, vol. 348, pp. 593-600, 2003.
Hirschi et al., "Assessing Identity, Phenotype, and Fate of Endothelial Progenitor Cells," *Arterioscler. Thromb. Vasc. Biol.*, vol. 28, pp. 1584-1595, 2008.
Ingber et al., "How Does Extracellular Matrix Control Capillary Morphogenesis?" *Cell*, vol. 58, pp. 803-805, 1989.
Ingber et al., "Mechanochemical Switching between Growth and Differentiation during Fibroblast Growth Factor-stimulated Angiogenesis In Vitro: Role of Extracellular Matrix," *J. Cell Biol.*, vol. 109, pp. 317-330, 1989.
Ingber, "Mechanical Signaling and the Cellular Response to Extracellular Matrix in Angiogenesis and Cardiovascular Physiology," *Circ. Res.*, vol. 91, pp. 877-887, 2002.
Ingram et al., "Identification of a novel hierarchy of endothelial progenitor cells using human peripheral and umbilical cord blood," *Blood*, vol. 104, pp. 2752-2760, 2004.
Ingram et al., "Vessel wall-derived endothelial cells rapidly proliferate because they contain a complete hierarchy of endothelial progenitor cells," *Blood*, vol. 105, No. 7, pp. 2783-2786, 2005.
International Search Report issued for PCT/US2009/068479 dated Sep. 2, 2010.
International Search Report issued in Application No. PCT/US2010/056268 dated Jul. 28, 2011.
Iruela-Arispe et al., "Cellular and Molecular Mechanisms of Vascular Lumen Formation," *Dev Cell.*, vol. 16, pp. 222-231, 2009.
Ispanovic et al., "Cdc42 and RhoA have opposing roles in regulating membrane type 1-matrix metalloproteinase localization and matrix metalloproteinase-2 activation," *Am. J. Physiol. Cell Physiol.*, vol. 295, pp. C600-C610, 2008.
Jaffe et al., "Rho GTPases: Biochemistry and Biology," *Annu. Rev. Cell Dev. Biol.*, vol. 21, pp. 247-269, 2005.
Kamei et al., "Endothelial tubes assemble from intracellular vacuoles In vivo," *Nature*, vol. 442, pp. 453-456, 2006.
Kaya et al., "VEGF protects brain against focal ischemia without increasing blood-brain permeability when administered intracerebroventicularly," *J. Cereb. Blood. Flow. Metab.*, vol. 25, pp. 1111-1118, 2005.
Khetan et al., "Cellular Encapsulation in 3D Hydrogels for Tissue Engineering," *Vis. Exp.*, (32), pp. 1-4, 2009.
Khetan et al., "Sequential crosslinking to control cellular spreading in 3-dimensional hydrogels," *Soft Matter*, vol. 5, No. 8, pp. 1601-1606, 2009.
Khetan et al., "Tuning Hydrogel Properties for Applications in Tissue Engineering," *Conf. Proc. IEEE Eng. Med. Biol. Soc.*, vol. 1, pp. 2094-2096, 2009.
Kilarski et al., "Biomechanical regulation of blood vessel growth during tissue vascularization," *Nat. Med.*, vol. 15, pp. 657-664, 2009.
Kniazeva et al., "Endothelial cell traction and ECM density influence both capillary morphogenesis and maintenance in 3-D," *Am. J. Physiol. Cell Physiol.*, vol. 297, No. 1, pp. C179-C187, 2009.

(56) References Cited

OTHER PUBLICATIONS

Leslie-Barbick et al., "Covalently-Immobolized Vascular Endothelial Growth Factor Promotes Endothelial Cell Tubulogensis in Poly-(ethylene glycol) Diacrylate Hydrogels," *Journal of Biomaterials Science, Polymer Edition*, vol. 20, No. 12, pp. 1763-1779, 2009.
Li et al., "VEGF and PlGF promote adult vasculogenesis by enhancing EPC recruitment and vessel formation at the site of tumor neovascularization," FASEB J., vol. 20, pp. 1495-1497, 2006.
Lo et al., "Cell Movement Is Guided by the Rigidity of the Substrate," *Biophys. J.*, vol. 79, pp. 144-152, 2000.
Lubarsky et al., "Tube Morphogenesis: Making and Shaping Biological Tubes," *Cell*, vol. 112, pp. 19-28, 2003.
Lutolf et al., "Synthetic biomaterials as instructive extracellular microenvironments for morphogenesis in tissue engineering," *Nature Biotechnology*, vol. 23, No. 1, pp. 47-55, 2005.
Lutolf et al., "Synthetic matrix metalloproteinase-sensitive hydrogels for the conduction of tissue regeneration: Engineering cell-invasion characteristics," *Proc. Natl. Acad. Sci. U S. A.*, vol. 100, No. 9, pp. 5413-5418, 2003.
Mammoto et al., "A mechanosenstivie transcriptional mechanism that controls angiogenesis," *Nature*, vol. 457, pp. 1103-1108, 2009.
Mammoto et al., "Rho signaling and mechanical control of vascular development," *Curr. Opin. Hematol.*, vol. 15, pp. 228-234, 2008.
Matthews et al., "Cellular adaptation to mechanical stress: role of integrins, Pho, cytoskeletal tension and mechanosensitive ion channels," *J. Cell Sci.*, vol. 119, pp. 508-518, 2006.
McBeath et al., "Cell Shape, Cytoskeletal Tension, and RhoA Regulate Stem Cell Lineage Commitment", *Dev. Cell.*, vol. 6, pp. 483-495, 2004.
Mead et al., "Isolation and Characterization of Endothelial Progenitor Cells from Human Blood," *Current protocols in stem cell biology*, vol. 6, pp. 2C.1.1-2C.1.27, 2008.
Melero-Martin et al., "Engineering Robust and Functional Vascular Networks In Vivo With Human Adult and Cord Blood-Derived Progenitor Cells," *Circulation Research*, vol. 103, No. 2, pp. 194-202, 2008.
Moon et al., "Biomimetic hydrogels with pro-angiogenic properties," *Biomaterials*, vol. 31, No. 14, pp. 3840-3847, 2010.
Moore et al., "Control of Basement Membrane Remodeling and Epithelial Branching Morphogenesis in Embryonic Lung by Rho and Cytoskeletal Tension," *Dev. Dyn*,. vol. 232, pp. 268-281, 2005.
Muslim et al., "Synthesis and bioactivities of poly(ethylene glycol)-chitosan hybrids," *Carbohydrate Polymers*, vol. 46. pp. 323-330, 2001.
Pelham et al., "Cell locomotion and focal adhesions are regulated by substrate flexibility," *Proc. Natl. Acad. Sci. U. S. A.*, vol. 94, pp. 13661-13665, 1997.
Peppas et al., "The structure of highly crosslinked poly(2-hydroxyethyl methacrylate) hydrogels," *Journal of Biomedical Materials Research*, vol. 19, pp. 397-411, 1985.
Perkins et al., "Conventional and Immunoelectron Microscopy of Mitchondria," *Methods Mol. Biol.*, vol. 372, pp. 467-483, 2007.
Prater et al., "Working hypothesis to redefine endothelial progenitor cells," *Leukemia*, vol. 21, pp. 1141-1149, 2007.
Raeber et al., "Molecularly Engineered PEG Hydrogels: A Novel Model System for Proteolytically Mediated Cell Migration," *Biophysical Journal*, vol. 89, No. 2, pp. 1374-1388, 2005.
Romanic et al., "Matrix Metalloproteinase Expression Increases After Cerebral Focal Ischemia in Rats: Inhibition of Matrix Metalloproteinase-9 Reduces Infarct Size," *Stroke*, vol. 29, pp. 1020-1030, 1998.
Sacharidou et al., "Endothelial lumen signaling complexes control 3D matrix-specific tubulogenesis through interdependent Cdc42- and MT1-MMP-mediated events," *Blood*, vol. 115, No. 25, pp. 5259-5269, 2010.
Saunders et al., "Coregulation of vascular tube stabilization of endothelial cell TIMP-2 and pericyte TIMP-3," *J. Cell Biol.*, vol. 175, pp. 179-191, 2006.
Schatteman et al., "Blood-derived angioblasts accelerate blood-flow restoration in diabetic mice," *J. Clin. Invest.*, vol. 106, pp. 571-578, 2000.
Seliktar et al., "MMP-2 senstive, VEGF-bearing bioactive hydrogels for promotion of vascular healing," *J. Biomed. Mater. Res. A*, vol. 68, No. 4, pp. 704-716, 2004.
Shepherd et al., "Vascularization and engraftment of a human skin substitute using circulating progenitor cell-derived endothelial cells," *FASEB J.*, vol. 20, pp. 1739-1741, 2006.
Shu et al., "Synthesis and evaluation of injectable, in situ crosslinkable synthetic extracellular matrices for tissue engineering," *J. Biomed. Mater. Res. A*, vol. 79, pp. 902-912, 2006.
Sieminski et al., "Primary sequence of ionic self-assembling peptide gels affects endothelial cell adhesion and capillary morphogenesis," *Journal of Biomedical Materials Research*, vol. 87A, No. 2, pp. 494-504, 2008.
Sieminski et al., "The relative magnitudes of endothelial force generation and matrix stiffness modulate capillary morphogenesis in vitro," *Exp. Cell. Res.*, vol. 297, pp. 574-584, 2004.
Sieminski et al., "The Stiffness of Three-dimensional Ionic Self-assembling Peptide Gels Affects the Extent of Capillary-like Network Formation," *Cell Biochem. Biophys.*, vol. 49, pp. 73-83, 2007.
Silva et al., "Material-based deployment enhances efficacy of endothelial progenitor cells," *Proceedings of the National Academy of Sciences*, vol. 105, No. 38, pp. 14347-14352, 2008.
Stephanou et al., "The rigidity in fibrin gels as a contributing factor to the dynamics of in vitro vascular cord formation," *Microvascular Research*, vol. 73, No. 3, pp. 182-190, 2007.
Stratman et al., "Endothelial cell lumen and vascular guidance tunnel formation requires MT1-MMP-dependent proteolysis in 3-dimensional collagen matrices," *Blood*, vol. 114, No. 2, pp. 237-247, 2009.
Sun et al., "VEGF-induced neuroprotection, neurogenesis, and angiogenesis after focal cerebral ischemia," *J. Clin. Invest.*, vol. 111, pp. 1843-1851, 2003.
Timmermans et al., "Endothelial progenitor cells: identity defined?" *J. Cell. Mol. Med.*, vol. 13, pp. 87-102, 2009.
Toole, "Hyaluronan in morphogenesis," *Semin. Cell. Dev. Biol.*, vol. 12, No. 2, pp. 79-87, 2001.
Toole, "Hyaluronan: From Extracellular Glue to Pericellular Cue," Nat Rev Cancer, vol. 4, No. 7, pp. 528-539, 2004.
Van Hinsbergh et al., "Pericellular Proteases in Angiogenesis and Vasculogenesis," *Arterioscler. Thromb. Vasc. Biol.*, vol. 26, pp. 716-728, 2006.
Vanderhooft et al., "Rheological Properties of Cross-Linked Hyaluronan-Gelatin hydrogels for Tissue Engineering," *Macromolecular Bioscience*, vol. 9, No. 1, pp. 20-28, 2009.
Wang et al., "A tough biodegradable elastomer," *Nature Biotechnology*, vol. 20, No. 6, pp. 602-660, 2002.
Wang et al., "In vivo degradation characteristics of poly(glycerol sebacate)," *Journal of Biomedical Materials Research*, vol. 66A, No. 1, pp. 192-197, 2003.
Won et al., in: Biomaterials & Engineering Handbook, D. L. Wise (Ed.), p. 356. Marcel Dekker, New York, NY (2000) (3 pages).
Written Opinion of the International Searching Authority issued in Application No. PCT/US2009/068479 dated Sep. 2, 2010.
Written Opinion of the International Searching Authority issued in Application No. PCT/US2010/056268 dated Jul. 28, 2011.
Written Opinion of the International Searching Authority issued in Application No. PCT/US2012/034802 dated Nov. 26, 2012.
Xu et al., "Proteolytic exposure of a cryptic site within collagen type IV is required for angiogenesis and tumor growth in vivo," *The Journal of Cell Biology*, vol. 154, No. 5, pp. 1069-1080, 2001.
Yoder et al., "Redefining endothelial progenitor cells via clonal analysis and hematopoietic stem/progenitor cell principals," *Blood*, vol. 109, pp. 1801-1809, 2007.
Yoder, "Defining human endothelial progenitor cells," *Journal of Thrombosis and Haemostasis*, vol. 7, Suppl. 1, pp. 49-52, 2009.
Yoder, "Is Endothelium the Origin of Endothelial Progenitor Cells?" *Arterioscler. Thromb. Vasc. Biol.*, vol. 30, No. 6, pp. 1094-1103, 2010.

(56) References Cited

OTHER PUBLICATIONS

Zaman et al., "Migration of tumor cells in 3D matrices is governed by matrix stiffness along with cell-matrix adhesion and proteolysis," *Proceedings of the National Academy of Sciences*, vol. 103, No. 29, pp. 10889-10894, 2006.
Zhang et al., "Novel Biodegradable and thermosensitive dex-ai/pnipaam hydrogel," *Macromolecular Bioscience*, vol. 3, pp. 87-91, 2003.
Zhang et al., "Temperature sensitive dendrite-shaped pnjp/am/dex-ai hybrid hydrogel particles: formulation and properties," *European Polymer Journal*, vol. 40, pp. 2251-2257, 2004.
Balakrishnan et al., *Biomaterials*, vol. 26, No. 32, pp. 6335-6342, 2005.
Boucard et al. *Biomaterials*, vol. 28, No. 24, pp. 3478-3488, 2007.
Cubison et al., *Burns*, vol. 32, No. 8, pp. 992-999, 2006.
Ehrbar et al., *Circ Res*, vol. 94, No. 8, pp. 1124-1132, 2004.
Extended European Search Report issued in European Application No. 10830680.4 dated Jun. 2, 2014.
Extended European Search Report issued in European Application No. 12786297.7 dated Jan. 12, 2015.
Fagenholz et al., *J Burn Care Res*, vol. 28, No. 5, pp. 681-690, 2007.
Flamme et al., *Developmental Biology*, vol. 169, No. 2, pp. 699-712, 1995.
Fox et al., *British Journal of Surgery*, vol. 95, No. 2, pp. 244-251, 2008.
Gill et al., *Circ Res* vol. 88, No. 2, pp. 167-174, 2001.
Greenhalgh, The International Journal of Biochemistry & Cell Biology, vol. 30, No. 9, pp. 1019-1030, 1998.
Gurtner et al., Nature, vol. 453, No. 7193, pp. 314-321, 2008.
Hanjaya-Putra D, et al., Blood, vol. 118, No. 3, pp. 804-815, 2011.
Haroon et al., The FASEB Journal, vol. 13, No. 13, pp. 1787-1795, 1999.
Hu et al., Int. J. Biochem. Cell. Biol., 2002, vol. 34, p. 396-402.
Inoue et al., PLoS ONE, vol. 3, No. 8, p. e3068, 2008.
Ismail et al., Cardiovasc Pathol, vol. 12, No. 2, pp. 82-90, 2003.
Ito et al., Nature, vol. 447, No. 7142, pp. 316-320.
Khetan et al., Soft Matter, vol. 5, No. 8, pp. 1601-1606, 2009.
Kim et al., Biomaterials, vol. 30, No. 22, pp. 3742-3748, 2009.
Kim et al., J Invest Dermatol, vol. 128, No. 7, pp. 1812-1820, 2008.
Kirker et al., Biomaterials, vol. 23, No. 17, pp. 3661-3671, 2002.
Kiyozumi et al., Burns, vol. 33, No. 5, pp. 642-648, 2007.
Kiyozumi et al., *Journal of Biomedical Materials Research Part B: Applied Biomaterials*, vol. 79B, No. 1, pp. 129-136, 2006.
Kloxin et al., *Science*, vol. 324, No. 5923, pp. 59-63, 2009.
Kurisawa et al., "Modulated degradation of dextran hydrogels grafted with poly(N-isoproprylacrylamide-co-N,N-dimethylacrylamide) in response to temperature," Macromolecular Chemistry and physics, 199(11), pp. 2613-2618, 1998.
Lee et al., *Mol Ther*, vol. 15, No. 6, pp. 1189-1194, 2007.
Li et al., *Microscopy Research and Technique*, vol. 60, No. 1, 107-114, 2003.
Light et al., *J Burn Care Rehabil*, vol. 25, No. 1, pp. 33-44, 2004.
Liu et al., Biomaterials, vol. 30, No. 8, pp. 1453-1461, 2009.
Lombardo et al., "Crosslinked Carboxymethylcellulose Hydrogels: Versatile Platforms for Studying Cellular Behaviour in 3D Biomaterials." Transactions of the 32nd Annual Meeting of the Society for Biomaterials, vol. 30:25, 2007, Annual Meeting. http//jleachlab.org/people/lombardo.html (May 12, 2015). 2 printed pages.
Madsen et al., Biomacromolecules, vol. 9, No. 8, pp. 2265-2275, 2008.
Martin, Science, vol. 276, No. 5309, pp. 75-81, 1997.
Millius et al., Methods Mol. Biol., vol. 571, pp. 167-177, 2009.
Muslim et al., Carbohydr. Polym., 2001, vol. 46. p. 323-330.
Office Action issued in U.S. Appl. No. 14/115,237 dated Jun. 24, 2015.
Office Action issued in U.S. Appl. No. 14/115,237 dated Nov. 6, 2015.
Peichev et al., Blood, vol. 95, No. 3, pp. 952-958, 2000.
Puolakkainen et al., Journal of Surgical Research, vol. 58, No. 3, pp. 321-329, 1995.
Sase et al., J Cell Sci, vol. 122, No. 18, pp. 3303-3311, 2009.
Schulz et al., Annual Review of Medicine, vol. 51, No. 1, pp. 231-244, 2000.
Sen et al., J. Burn Care Res., vol. 31, No. 6, pp. 836-848, 2010.
Shepherd et al., Biomaterials, vol. 32, No. 1, pp. 258-267, 2011.
Shu et al., "Attachment and spreading of fibroblasts on an RGD peptide-modified injectable hyaluronan hydrogel," J. Biomed Materials Research, vol. 68, No. 2, 2004.
Sibal et al., Diabetologia, vol. 52, No. 8, pp. 1464-1473, 2009.
Singer et al., New England Journal of Medicine, vol. 341, No. 10, pp. 738-746, 1999.
Steed, Surgical Clinics of North America, vol. 77, No. 3, pp. 575-586, 1997.
Sun et al., "Dextran hydrogel scaffolds enhance angiogenic responses and promote complete skin regeneration during burn wound healing," PNAS, 2011, vol. 108, No. 52, pp. 20976-20981.
Sun et al., Biomaterials, vol. 32, No. 1, pp. 95-106, 2011.
Sun et al., Journal of Biomedical Materials Research Part A, vol. 93A, No. 3, pp. 1080-1090, 2010.
Tibbs, Radiotherapy and Oncology, vol. 42, No. 2, pp. 99-106, 1997.
Tredget, Journal of Trauma-Injury Infection and Critical Care, vol. 62, No. 6, pp. S69-S69, 2007.
Zhang et al., "A novel PH- and ionic-strength-sensitive carboxy methyl dextran hydrogel." Biomaterials, vol. 26, 2005, pp. 4677-4683.
Zhang et al., Arch Surg, vol. 145, No. 3, pp. 259-266, 2010.
Zhang et al., Biomaterials, 2002, vol. 23, pp. 2641-2648.
Zhang et al., Wound Repair Regen., vol. 18, No. 2, pp. 193-201, 2010.

\* cited by examiner

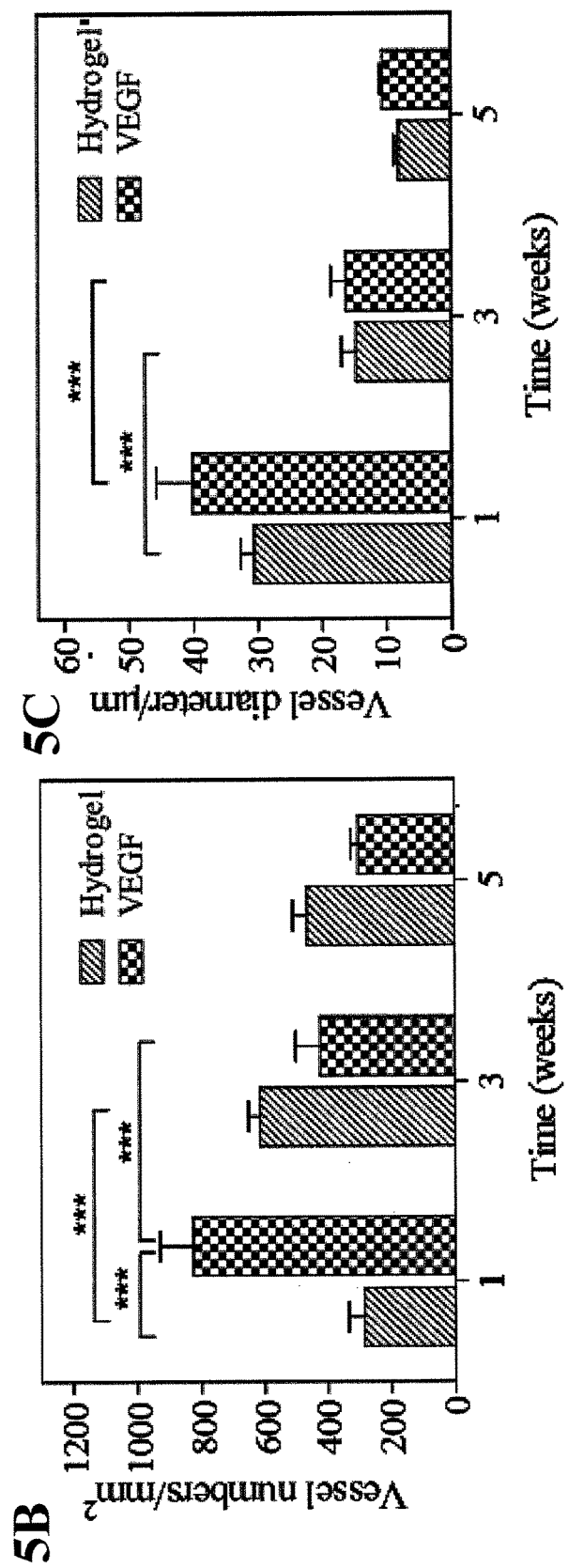
Figure 5 – cont.

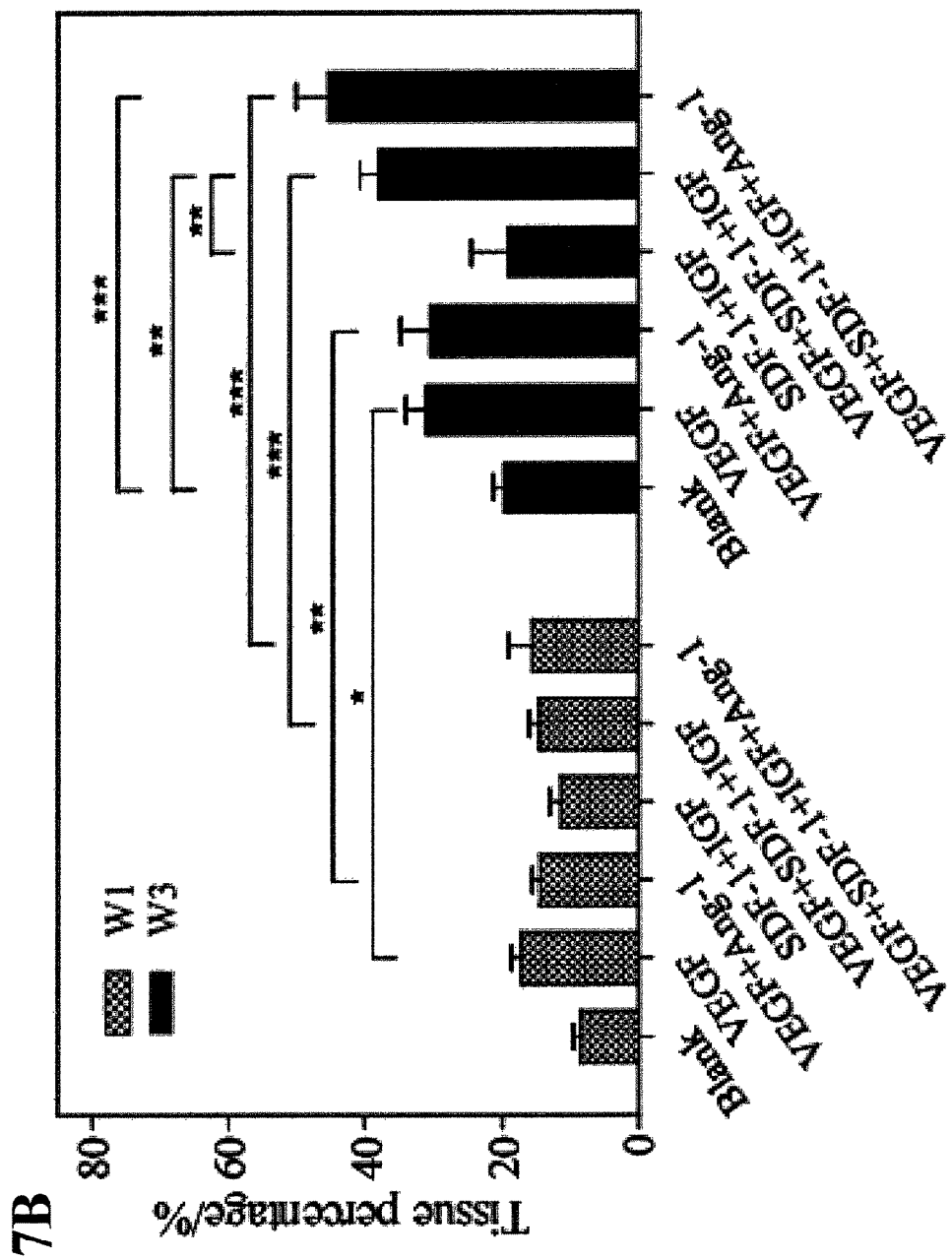
Figure 7 – cont.

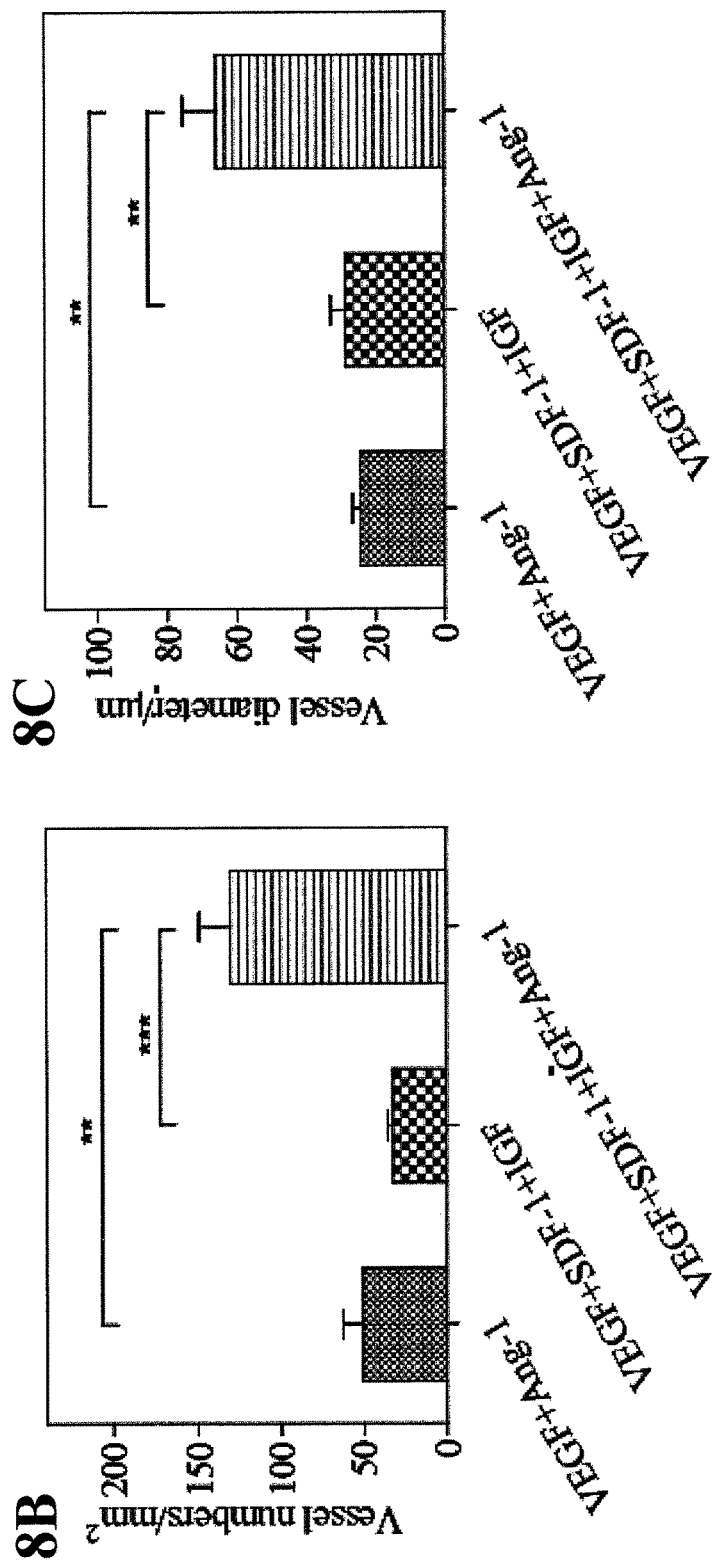
Figure 8 – cont.

FUNCTIONAL VASCULARIZATION WITH BIOCOMPATIBLE POLYSACCHARIDE-BASED HYDROGELS

CROSS-REFERENCE TO RELATED APPLICATION

This application is a National Stage Application under 35 U.S.C. § 371 of PCT/US2011/042671, filed on Jun. 30, 2011, which claims priority to U.S. Provisional Application No. 61/360,178, filed on Jun. 30, 2010, the entire content of each of which is hereby incorporated by reference.

BACKGROUND

Field of the Invention

The present invention is related to implanted compositions with vascular endothelial growth factor (VEGF) in combination with other growth factors.

Background of the Invention

A healthy blood circulatory system is pivotal to the development and maintenance of functional tissues and organs; damaged blood vessels or compromised circulation can result in ischemic tissue with limited intrinsic regeneration potential (Kraehenbuehl et al., Biomaterials vol. 30, no. 26, pp. 4318-24, 2009). The ideal treatment for vascular damage is the regeneration of autologous blood vessels, which can be optimized by cell engineering (Srivastava et al. Nature vol. 441, no. 7079, pp. 1097-9, 2006; Adams et al., Trends in Cardiovascular Medicine, vol. 17, no. 7, pp. 246-51, 2007; Sales et al., Trends Biotechnol, vol. 23, no. 9, pp. 461-7, 2005) and extracellular matrix manipulation (Sun et al., Regenerative Medicine, vol. 3, no. 3, 435-47, 2009; Yang et al., Tissue Engineering vol. 7, no. 6, 679-89, 2001; Ravi et al., Regenerative Medicine vol. 5, no. 1, 107-20, 2010). Vascular regeneration, however, remains a complex process which includes the mobilization, chemotaxis, adhesion, proliferation, and differentiation of progenitor cells (Guiducci et al., vol. 47, suppl. 5, pp. v18-20, 2008); further, the process is influenced by tissue composition and, possibly, inflammation induced by tissue injury.

Research has uncovered a broad range of pharmaceutical and biomedical applications for polymeric hydrogels, due to their three-dimensional (3D) structural and mechanical similarity to the native ECM of many tissues. Optimally tailored biodegradable polymer hydrogel scaffolds could provide a constant delivery of bioactive angiogenic factors, advancing therapeutic vascularization. Moreover, these porous hydrogel scaffolds permit circulating cells to infiltrate into them to degrade them, thereby releasing entrapped growth factors (GFs) and facilitating neovascularization (Sheridan et al., J Controlled Release, vol. 64, no. 1-3, pp. 91-102, 2000; Perets et al., J Biomed Mater Res Part A, vol. 65A, no. 4, pp. 489-97, 2003). For in vivo transplantation purposes, the hydrogel scaffold should have enough mechanical strength to maintain the integrity of its porous structure during the vascularization process. Overall, a porous hydrogel scaffold capable of a constant release of GFs, proper mechanical strength, and rapid degradation may enable vascular engineering.

Polysaccharide-based hydrogels are non-toxic and biodegradable. From a structural point of view, polysaccharides have reactive functional groups that can be modified to form hydrogels with specific characteristics of interest. In recent years, hyaluronan-based hydrogels have been extensively investigated as scaffolds to stimulate in vivo angiogenesis (Riley et al., Biomaterials vol. 27, no. 35, pp. 5935-43, 2006; Elia et al., Biomaterials, vol. 31, no. 17, pp. 4630-8, 2010; Hosack et al., Biomaterials vol. 29, no. 15, 2336-47, 2008; Pike et al., Biomaterials, vol. 27, no. 30, pp. 5242-51, 2006); these hydrogels were manipulated to deliver different angiogenic factors to improve neovascularization. Lee et al. demonstrated that a VEGF-encapsulated alginate hydrogel scaffold promoted angiogenesis (Lee et al., Nature, vol. 408, no. 6815, 998-1000, 2000). However, they reported that little to no tissue or blood vessel ingrowth into these hydrogel scaffolds occurred. Recently, the Cohen group reported that the in vivo prevascularization of an alginate scaffold improved therapeutic vascularization (Dvir et al., Proc Natl Acad Sci USA, vol. 106, no. 35, 14990-5, 2009). Although dextran-based hydrogels have been investigated for various purposes (Bos et al., Biomaterials vol. 26, no. 18, pp. 3901-9, 2005; Ferreira et al., Biomaterials vol. 28, no. 17, pp. 2706-17, 2007), their potential for in vivo therapeutic vascularization has not been fully explored.

Although many different types of polymeric hydrogels have been developed since the 1950s (Kopecek, J. Nature 2002, vol. 417, pp. 388-391), they all fall into one of two basic categories of polymer: natural or synthetic. Natural polymers have gained interest over the past few decades because of their biocompatibility and the presence of biologically recognizable groups to support cellular activities (Van Tomme et al. Expert Rev. Med. Dev. 2007, vol. 4, pp. 147-164). Among the natural polymers, dextran is a colloidal, hydrophilic, biocompatible, and nontoxic polysaccharide composed of linear $\alpha$-1,6-linked D-glucopyranose residues with a low fraction of $\alpha$-1,2, $\alpha$-1,3 and $\alpha$-1,4 linked side chains. Also, dextran can be biodegraded by dextranase, which exists in mammalian (including human) tissues. From a structural point of view, dextran has reactive hydroxyl groups (i.e. —OH) that can be modified to form hydrogels via crosslinking by photochemical and other means. As dextran is naturally resistant to protein adsorption and cell adhesion, modification of its polymer backbone allows development of a hydrogel with specific characteristics. Because of these properties, dextran and its hybrids have been extensively investigated as drug and/or gene carriers. For examples, dextran-based biomaterials have been employed in cell immobilization (Massia et al., Biomaterials, 2000, vol. 21, pp. 2253) and gene transfection (Azzam et al., Macromol. Symp., 2003, vol. 195, p. 247) and as carriers for a variety of pharmaceutically active drugs (de Jong et al., Macromolecules, 2000, vol. 33, p. 3680; Kim et al., J. Biomater. Appl., 2000, vol. 15, p. 23; Won et al., Carbohydr. Polym., 1998, vol. 36, p. 327; Kim et al., Arch. Pharma. Res., 2001, vol. 24, p. 69; Chu, C. C., in: Biomaterials Handbook—Advanced Applications of Basic Sciences, and Bioengineering, D. L. Wise (Ed.), p. 871. Marcel Dekker, New York, N.Y. (2003); Won et al., in: Biomaterials & Engineering Handbook, D. L. Wise (Ed.), p. 356. Marcel Dekker, New York, N.Y. (2000); Zhang et al., J. Biomater. Appl., 2002, vol. 16, p. 305; Peppas et al., Europ. J. Pharma. Biopharma., 2000, vol. 50, p. 27; Van Tomme et al., Biomaterials, 2006, vol. 27, p. 4141).

Many attempts have been made to engineer dextran-based polymers for various applications (Heinze et al., In Polysaccharides Ii, Springer-Verlag Berlin: Berlin, 2006; p. 199). Van Tomme et al. recently reviewed both chemically and physically crosslinked dextran-based hydrogels that were developed for protein release (Van Tomme et al. Expert Rev. Med. Dev. 2007, vol. 4, pp. 147-164). To generate chemically crosslinked dextran hydrogels, the major modification challenge is to introduce polymerizable bonds for efficient crosslinking. A common approach is to incorporate vinyl groups via different types of acrylates, thus enabling photocrosslinking. Such acrylates include glycidyl acrylate (Edman, et al., *I. J. Pharm. Sci.* 1980, vol. 69, pp. 838-842), glycidyl methacrylate (Vandijkwolthuis et al., *Macromolecules,* 1995, vol. 28, pp. 6317-6322), methacrylate (Kim et al., *J. Biomed. Mater. Res.,* 2000, vol. 53, pp. 258-266; Ferreira et al., *Biomaterials,* 2007, vol. 28, pp. 2706-2717), acrylate (Zhang et al., *J. Polym. Sci. Polym. Chem.,* 1999, vol. 37, pp. 4554-4569) and hydroxyethyl methacrylate (vanDijkWolthuis et al., *Macromolecules,* 1997, vol. 30, pp. 4639-4645; vanDijkWolthuis et al., *Polymer,* 1997, vol. 38, pp. 6235-6242). These hydrogels were proven to be efficient protein carriers. Chu et al. also developed maleic-anhydride- and allyl-isocyanate- (AI-) based dextran hydrogels (Kim et al., *J. Biomed. Mater. Res.,* 2000, vol. 53, pp. 258-266; Zhang et al., *J. Polym. Sci. Polym. Chem.,* 2000, vol. 38, pp. 2392-2404), which were shown to have tunable properties. Other than UV photocrosslinking, the Schiff reaction has also been employed to form crosslinks by oxidizing dextran rings into aldehyde groups (Maia et al., "Synthesis and characterization of new injectable and degradable dextran-based hydrogels," *Polymer,* 2005, vol. 46, pp. 9604-9614; Ito et al., *Biomaterials,* 2007, vol. 28, pp. 3418-3426).

One approach to preparing dextran-based hydrogels involves the use of a synthetic polymer precursor so that the resulting hydrogels can have both synthetic and naturally occurring polymers within a single entity. Among synthetic polymer precursors that couple with dextran, poly(ethylene glycol) (PEG) is popular because it is a unique amphiphilic, biocompatible but non-biodegradable polymer, and has been explored for many biomedical applications. Although PEG is not biodegradable, lower molecular weight PEG can be readily excreted from the body via kidney and liver, thereby making it more suitable for drug delivery. In addition, PEG has also been employed to improve biocompatibility (Zhang et al., *Biomaterials,* 2002, vol. 23, p. 2641-2648; Chung et al., *Int. J. Biol. Macromol.,* 2003, vol. 32, p. 17), promote peptide immobilization (Hem et al., *J. Biomed. Mater. Res.,* 1998, vol. 39. p. 266; Wang et al., *J. Membr. Sci.,* 2002, vol. 195, p. 103), prolong protein drug circulating time (Koumenis et al., *Int. J. Pharma.,* 2000, vol. 198, p. 83; Greenwald et al., *Adv. Drug Deli. Rev.,* 2003, vol. 55, p. 217), increase bioactivity (Muslim et al., *Carbohydr. Polym.,* 2001, vol. 46. p. 323-330) and reduce immunogenicity (Hu et al., *Int. J. Biochem. Cell. Biol.,* 2002, vol. 34, p. 396-402).

SUMMARY

Embodiments include compositions having VEGF, at least one additional growth factor, and an implant carrier. In some embodiments, the additional growth factor may be an angiogenic growth factor. In some embodiments, the additional growth factor may be, for example, angiopoietin, stromal cell-derived factor, insulin-like growth factor, platelet-derived growth factor, stem cell factor and combinations thereof. In some embodiments, the additional growth factor is angiopoietin or angiopoietin-1. In some embodiments, the additional growth factor is a combination of stromal cell-derived factor and insulin-like growth factor. In some embodiments, the additional growth factor is a combination of angiopoietin, stromal cell-derived factor, and insulin-like growth factor.

In some embodiments, the implant carrier is a hydrogel. The implant carrier may be, for example, a polysaccharide-based hydrogel or a dextran-based hydrogel. In some embodiments, the implant carrier is a dextran-based hydrogel where the dextran has a degree of substitution less than about 0.2.

Embodiments include compositions having VEGF, at least one additional growth factor and a polysaccharide with at least one monomer having at least one substituted hydroxyl group, wherein the substituted hydroxyl group has the formula (III)

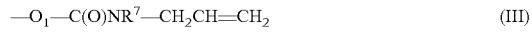
—O₁—C(O)NR⁷—CH₂CH=CH₂ (III)

and $O_1$ is the oxygen atom of said substituted hydroxyl group and $R^7$ is hydrogen or $C_1$-$C_4$ alkyl. In some embodiments, $R^7$ is hydrogen. In some embodiments, the degree of substitution on the polysaccharide is less than about 0.2.

In some embodiments, the polysaccharide further has a second substituted hydroxyl group having the formula (IV), where formula (III) and formula (IV) are different, and the substituted hydroxyl group of formula (III) and formula (IV) may be on the same or different monomers. Formula (IV) is

Y—(CR²R³)ₙ—NR⁴R⁵ (IV)

where Y is —O₁— or —O₁C(O)—, or —O₁C(O)NR¹—, and $O_1$ is the oxygen atom of said substituted hydroxyl group. $R^1$ is hydrogen or $C_1$-$C_4$ alkyl and n=1, 2, 3, or 4. $R^4$ and $R^5$ are independently hydrogen or $C_1$-$C_4$ alkyl. $R^2$ and $R^3$ are independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring.

In some embodiments, at least one hydroxyl-substituted saccharide monomer in the polysaccharide is a glucopyranose monomer. In some embodiments, the polysaccharide is dextran. In some embodiments, the dextran has an average molecular weight of at least 20,000.

In some embodiments, the composition further comprises a second crosslinkable molecule. In some embodiments, the second crosslinkable molecule is poly(ethylene glycol) diacrylate. In some embodiments, the poly(ethylene glycol) diacrylate has a molecular weight of at least 2000.

Embodiments include compositions prepared by crosslinking any of the above compositions. Compositions may be crosslinked chemically or photochemically.

Embodiments include hydrogels prepared by crosslinking any of the above compositions. Some embodiments include hydrogels prepared by crosslinking compositions having poly(ethylene glycol) diacrylate.

Embodiments include methods of increasing neovascularization or tissue regeneration by administering to a subject in need a composition described herein. In some embodiments, the mode of administering is implanting. In other words, the composition is implanted in the subject. In some embodiments, increasing neovascularization increases tissue regeneration, increases healing of damaged tissues or organs or treats ischemia. In some embodiments, the method includes crosslinking the composition. The composition may be crosslinked prior to, or after administration.

Embodiments include methods of preparing compositions according to the invention by crosslinking any of the above crosslinkable compositions. In some embodiments, the crosslinkable composition further includes poly(etheylene glycol) diacrylate.

BRIEF DESCRIPTION OF THE DRAWINGS

FIG. 3A shows H&E staining of histological sections. FIG. 3B shows representative images of ED1 staining of week 3 explants. (Scale bars=100 µm)

FIG. 4A shows representative images of H&E staining of histological sections of Dex-AE/PEGDA, with and without VEGF implanted subcutaneously for 1, 3, and 5 weeks (W1, W3, W5). Arrows indicate the formation of giant cells, while the high-magnification insert reveals the formation of functional blood vessels with red blood cells. FIG. 5A shows α-SMA staining along the transplantation period of hydrogels with and without VEGF; arrows indicate vascular structures within the hydrogel after 5 weeks (W5). Quantification of the number (FIG. 5B) and size (FIG. 5C) of blood vessels surrounding the hydrogels along the 5-week transplantation period. Significance levels were set at: *$p<0.05$, $p<0.01$, and *$p<0.001$. Values shown are means±SD. Scale bars=100 µm

FIG. 7A shows representative images of H&E staining of histologic sections of Dex-AE/PEGDA after 1 and 3 weeks (W1, W3) without GFs (blank hydrogel) and with: VEGF; VEGF and Ang-1; SDF-1 and IGF; VEGF, SDF-1, and IGF; VEGF, SDF-1, IGF, and Ang-1. Arrows indicate functional blood vessels within the hydrogels. FIG. 7B shows quantification of the percentage of tissue ingrowth within the hydrogels. Significance levels were set at: *$p<0.05$, $p<0.01$, and *$p<0.001$. Values shown are means±SD. Scale bars=100 µm.

FIG. 8A shows representative images of H&E and α-SMA staining of histologic sections of Dex-AE/PEGDA after 3 weeks (W3) with: VEGF and Ang-1; VEGF, SDF-1, and IGF; and VEGF, SDF-1, IGF, and Ang-1. FIG. 8B shows quantification of blood vessel number and (C) diameter of newly induced blood vessels. Significance levels were set at: *$p<0.05$, $p<0.01$, and *$p<0.001$. Values shown are means±SD. Scale bars=100 µm.

DETAILED DESCRIPTION

Figure 1:
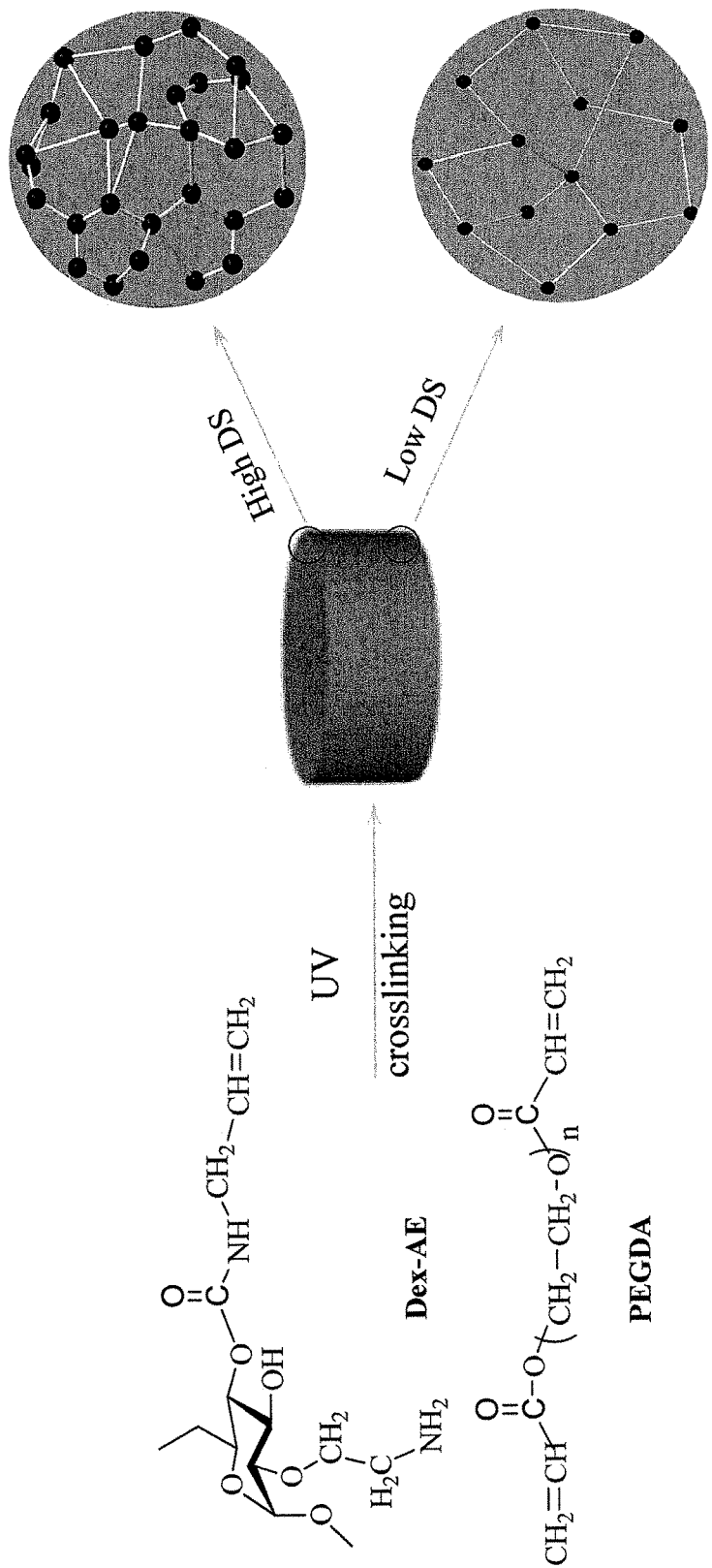
FIG. 1 shows preparation of dextran hydrogels with reduced degree of substitution (DS). Disk-shaped hydrogels are photocrosslinked from a solution of Dex-AE and PEGDA. Varying DS of Dex-AE are represented by the C=C double bonds in the chemical structure, and the crosslinked dots in the resulting hydrogel structures. Drawing not to scale.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated. Headings used herein are provided for clarity and organizational purposes only, and are not intended to limit the scope of the invention.

Definitions

By "disease" is meant any condition or disorder that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the term "implant" and its variations refer to the act of applying a composition or device below the surface of a body, or to the composition or device applied below the surface of a body, depending on context, and do not include applications to the body's surface. An implant carrier is an implant that releases materials incorporated therein after implantation.

As used herein, a "growth factor" is a protein, cytokine, or hormone that stimulates cellular growth, proliferation, differentiation, or structural formation.

By "subject" is meant an animal. In some embodiments, a subject may be a mammal, including, but not limited to, a human or non-human mammal, such as a bovine, equine, canine, ovine, or feline.

By "therapeutic delivery device" is meant any device that provides for the release of a therapeutic agent.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

The term "$C_1$-$C_4$ alkyl" as used herein means straight-chain, branched, or cyclic $C_1$-$C_4$ hydrocarbons which are completely saturated and hybrids thereof such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^c$Pr)), butyl (including n-butyl (n-Bu, $^n$Bu), iso-butyl (1-Bu, $^i$Bu), sec-butyl (s-Bu, $^s$Bu), tert-butyl (t-Bu, $^t$Bu), or cyclobutyl (c-Bu, $^c$Bu)), and so forth.

The term "3-6 membered ring" as used herein means a saturated, unsaturated, or aromatic ring having 3 to 6 atoms in the ring and at least two carbon atoms in the ring. Non-carbon atoms may include nitrogen, oxygen, sulfur, phosphorous and silicon. Some embodiments have 1 or 2 heteroatoms in the ring. In some embodiments, the 3-6 membered ring may be a "$C_3$ to $C_6$ ring" having 3-6 carbon atoms in the ring. Examples of 3-6 membered rings include cyclopropane, cyclopropene, epoxides, aziridine, tioepoxides, cyclobutane, cyclobutene, cyclobutadiene, oxetane, azetidine, thietane, cyclopentane, cyclopentene, cyclopentadiene, pyrrolidine, pyrroline, pyrrole, imidazole, tetrahydrofuran, dihydrofuran, furan, oxazole, oxadiazole, thiazole, thiadiazole, tetrahydrothiophene, dihydrothiophene, thiophene, cyclohexane, cyclohexene, cyclohexadiene, benezene, piperazine, pyridine, tetrahydropyran, pyran, thiane, thiopyran, morpholine, diazines (including pyridazines, pyrimidines, and pyrazines), and triazine rings.

A polysaccharide having at least one substituted hydroxyl group can also be referred to as a "modified polysaccharide."

As used herein, "monomer," "saccharide monomer unit," "saccharide monomer," and the like are used to refer to a single saccharide unit of a polysaccharide. Saccharide monomers bearing a substituent are referred to herein as "modified monomers" or "modified saccharide monomers" or "modified saccharide monomer units."

Compositions

Embodiments of the invention include compositions having Vascular Endothelial Growth Factor (VEGF) in combination with at least one additional growth factor and a delivery vehicle. As used herein, a delivery vehicle is a structural element, such as, for example, a microparticle (e.g. liposome or micelle), polymer, gel, and the like for delivery of VEGF and the at least one additional growth factor. The delivery vehicle may be suitable for administration locally or systemically. In some embodiments, the delivery vehicle is an implant carrier. When combined with an implant carrier, the combination of growth factors is administered locally. However, growth factors released from the composition may circulate throughout the body in some embodiments, but may also act locally to the site of administration.

The implant carrier may release the combination of VEGF and additional growth factor immediately after implantation, over an extended period of time (extended release), or after a period of time after implantation (delayed release).

The additional growth factor may be, for example, angiopoietin (ANG, such as angiopoietin-1 (ANG-1)), stromal cell-derived factor (SDF, such as stromal cell-derived factor-1 (SDF-1)), insulin-like growth factor (IGF, such as insulin-like growth factor-1 (IGF-1)), platelet-derived growth factor (PDGF), or stem cell factor (SCF), or combinations thereof. In some embodiments, the additional growth factor is angiopoietin-1. In some embodiment, the additional growth factor is a combination of stromal cell-derived factor-1 and insulin-like growth factor. In some embodiments, the additional growth factor is a combination of angiopoietin-1, stromal cell-derived factor-1 and insulin-like growth factor.

The implant carrier may be any drug delivery vehicle that releases proteins and is localized to specific location in the body. The implant carrier may be, for example, Micro/nano fiber mesh, lyposome, microparticle, metal or plastic implants coated with polymer, a hydrogel, non-hydrogel polymer, or other implantable matrix. In some embodiments, the implant carrier is a hydrogel. Examples of hydrogels include, for example, polysaccharide-based hydrogels, alginate hydrogels, hyaluronic acid hydrogels, collagen hydrogels, fibrin hydrogels, chitosan hydrogels and dextran-based hydrogels. In some embodiments, the implant carrier is a polysaccharide-based hydrogel. A polysaccharide-based hydrogel is a crosslinked hydrogel composition having greater than 10%, greater than 20%, or greater than 30% of a polysaccharide or modified polysaccharide. In some embodiments, the implant carrier is a dextran-based (a type of polysaccharide) hydrogel. Analogously, a dextran-based hydrogel is a crosslinked hydrogel composition having greater than 10%, greater than 20%, or greater than 30% dextran or modified dextran.

In embodiments, the percentage (by weight) of modified polysaccharide in the hydrogel may be greater than about 40%, greater than about 50%, greater than about 60% or greater than about 70%. In embodiments having a polysaccharide having a low degree of substitution of formula (III), described below, the composition may have a percentage (by weight) of modified polysaccharide of greater than about 80%.

In some embodiments, the polysaccharide-based hydrogel has a modified polysaccharide component with a degree of substitution less than about 0.2. "Degree of substitution" (DS) can be defined as the average number of substituted hydroxyl groups per saccharide monomer. A degree of substitution less than about 0.2 means that the number of substituted hydroxyl groups in the polysaccharide, divided by the total number of monomers in the polysaccharide is less than about 0.2.

In some embodiments, the modified polysaccharide is a polysaccharide where at least one hydroxyl-substituted saccharide monomer is a glucopyranose monomer. The glucopyranose monomer may be substituted at any available free hydroxyl group, or may be substituted on more than one available free hydroxyl group. The glucopyranose monomer may be incorporated into the polysaccharide in any suitable orientation, for example, via a 1,2-, 1,3-, 1,4-, 1,6-, or other linkage.

In some embodiments, the polysaccharide component of the polysaccharide-based hydrogel is dextran. In some embodiments, the dextran has an average molecular weight of at least about 20,000. The dextran may have an average molecular weight of at least about 30,000, at least about 40,000, at least about 50,000, or at least about 60,000. The dextran may have an average molecular weight less than about 200,000, less than about 150,000, or less than about 100,000. The dextran may have a molecular weight between any two endpoints. The molecular weight may expressed as the number average or weight average molecular weight. For instance, the dextran molecule may have an average molecular weight between about 20,000 and about 200,000, between about 20,000 and about 100,000 or between about 40,000 and about 70,000.

In some embodiments, the composition further comprises a protein, oligonucleotide, pharmaceutical agent, or cells. In general, any protein, oligonucleotide or pharmaceutical agent which may be delivered by a hydrogel may be delivered by the compositions of the present invention. Examples of proteins that may be delivered by hydrogels include bovine serum albumin (BSA) or ovalbumin. In some embodiments, the protein is a therapeutic protein, such as insulin or immunoglobulins (such as IgG). In some embodiments, the oligonucleotide is an antisense oligonucleotide. In some embodiments, the cells are stem cells.

In some embodiment, the polysaccharide-based hydrogel is formed from a composition having a modified polysaccharide, such as an acrylated polysaccharide, and poly(ethylene glycol) diacrylate. In some embodiments, the poly(ethylene glycol) diacrylate has a molecular weight of at least about 2000, at least about 4000, at least about 6000, at least about 8000, or at least about 10,000. In some embodiments, the poly(ethylene glycol) diacrylate has a molecular weight less than about 50,000, less than about 20,000, or less than about 15,000. The poly(ethylene glycol) diacrylate may have an a molecular weight of between any two previously disclosed endpoints. The molecular weight may be number average or weight average. In general, larger poly(ethylene glycol) polymers are cleared more slowly from the body by the kidneys. Larger poly(ethylene glycol) may result in hydrogels with a looser structure, larger pore size, and higher swelling. Persons skilled in the art can use routine experimentation to determine and select a poly(ethylene glycol) or poly(ethylene glycol) diacrylate to provide desired physical properties for a hydrogel according to the invention.

In some embodiments, the weight ratio between the polysaccharide or modified polysaccharide and poly(ethylene glycol) diacrylate is between about 10:1 and about 1:10. In other embodiments, the weight ratio of the polysaccharide and poly(ethylene glycol) diacrylate is between about 80:20 and 20:80. In other embodiments, the weight of the polysaccharide and poly(ethylene glycol) diacrylate is between about 70:30 and 30:70. In other embodiments, the weight ratio between the polysaccharide and poly(ethylene glycol) diacrylate is between about 60:40 and 40:60. In some embodiments, the weight ratio between the polysaccharide and poly(ethylene glycol) diacrylate is about 20:80, about 40:60, about 60:40, or about 80:20.

Hydrogel-Forming Compositions

Embodiments include a hydrogel-forming composition having Vascular Endothelial Growth Factor (VEGF) in combination with at least one additional growth factor and a hydrogel forming component.

A "hydrogel forming composition" as used herein means a composition capable of forming a solid hydrogel when crosslinked (chemically or photochemically), rather than a fluid-like gel. A "hydrogel forming component." is a chemical entity that forms a hydrogel upon crosslinking (chemically or photochemically). Persons skilled in the art will generally be able to distinguish a solid hydrogel from a fluid-like hydrogel. For instance, a "solid hydrogel" is capable of maintaining its shape after photocrosslinking, or has sufficient structure that mechanical properties, such as the modulus may be measured. By way of example, and not limitation, a solid hydrogel may be considered a hydrogel having an increase in mechanical strength. Alternatively, a solid hydrogel may be a gel with a modulus greater than about 200 Pa, greater than about 500 Pa, greater than about 700 Pa, or greater than about 1000 Pa.

Embodiments of the invention include hydrogel-forming compositions where the hydrogel-forming component is a polysaccharide with at least one monomer having at least one substituted hydroxyl group, wherein the substituted hydroxyl group has the formula (I):

$$—O_1—X \quad \text{(I)}$$

where $O_1$ is the oxygen atom of the substituted hydroxyl group, and X is a crosslinkable moiety.

In some embodiments, the substituted hydroxyl group has the formula (III):

$$—O_1—C(O)NR^7—CH_2CH=CH_2 \quad \text{(III)}$$

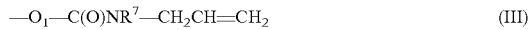

where $O_1$ is the oxygen atom of the substituted hydroxyl group and $R^7$ is hydrogen or $C_1$-$C_4$ alkyl. The hydrogel-forming composition may further include a second crosslinkable molecule. In some embodiments $R^7$ is H. In some embodiments, the second crosslinkable molecule is poly(ethylene glycol) diacrylate. In other embodiments, $R^7$ is H, and the second crosslinkable molecule is poly(ethylene glycol) diacrylate.

In some embodiments, the degree of substitution of hydroxyl groups on the polysacharide with formula (III) is about 0.2 or less.

In some embodiments, the hydrogel forming composition has at least about 40%, at least about 50%, at least about 60%, at least about 70% or at least about 80% of a polysaccharide having hydroxyl groups substituted by formula (III).

In some embodiments, the hydrogel-forming composition further includes up to about 20%, up to about 30%, up to about 40%, up to about 50%, or up to about 60% of a second crosslinkable molecule. In some embodiments, the second crosslinkable molecule is poly(ethylene glycol) diacrylate.

Other embodiments include a hydrogel forming composition where the hydrogel-forming component is a polysaccharide with a first substituted hydroxyl group of formula (III) and a second substituted hydroxyl group having the formula (IV):

$$Y—(CR^2R^3)_n—NR^4R^5 \quad \text{(IV)}$$

where Y is $—O_1—$ or $—O_1C(O)—$, or $—O_1C(O)NR^1—$; $O_1$ is the oxygen atom of said substituted hydroxyl group, $R^1$ is hydrogen or $C_1$-$C_4$ alkyl; n=1, 2, 3, or 4; $R^4$ and $R^5$ are independently hydrogen or $C_1$-$C_4$ alkyl; and $R^2$ and $R^3$ are independently hydrogen, $C_1$-$C_4$ alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring and formula (III) and formula (IV) are different. The substituted hydroxyl group of formula (III) and formula (IV) may be on the same or different monomers. In other embodiments, formula (IV) is $—O_1—(CH_2CH_2)—NH_2$.

Other embodiments include a hydrogel-forming compositions having at least about 80% of at least one polysaccharide or modified polysaccharide and up to about 20% poly(ethylene glycol) diacrylate, where the polysaccharide has a first substituted hydroxyl group having formula (III) a second substituted hydroxyl group having the formula (IV), where formula (III) and formula (IV) are different, and the substituted hydroxyl group of formula (III) and formula (IV) may be on the same or different monomers.

Polysaccharides with Low Degree of Substitution

In some embodiments, the hydrogel-forming composition includes a polysaccharide with at least one monomer having at least one substituted hydroxyl group, wherein the substituted hydroxyl group has the formula (III), and wherein the degree of substitution of formula (III) on the polysaccharide is less than about 0.2. As discussed previously, formula (III) is $—O_1—C(O)NR^7—CH_2CH=CH_2$ and $O_1$ is the oxygen atom of said substituted hydroxyl group and $R^7$ is hydrogen or $C_1$-$C_4$ alkyl. "Degree of substitution" (DS) can be defined as the average number of substituted hydroxyl groups per saccharide monomer. A degree of substitution less than about 0.2 means that the number of substituted hydroxyl groups having the structure of formula (III) in the polysaccharide, divided by the total number of monomers in the polysaccharide is less than about 0.2. The degree of substitution can be calculated from the NMR spectrum. For example, the ratio of the sum of the normalized, integrated intensities of the hydroxyl group peaks to the normalized, integrated intensities of the anomeric proton peak is subtracted from the number of unsubstituted hydroxyl groups in an unmodified monomer unit to determine the degree of substitution. For dextran polysaccharides, for example, each dextran monomer unit has three hydroxyl groups. If, for example, the sum of the integrated intensities of the hydroxyl peaks was 11, and the integrated intensity of the anomeric proton was 4, the ratio would be 2.75. This value (2.75) is subtracted from the total number of hydroxyls (3), to calculate the degree of substitution (3−2.75=0.25). This also corresponds to an average of one substituted hydroxyl group for every 4 monomer units. In some embodiments, the degree of substitution may be between about 0.01 and about 0.2. In other embodiments, the degree of substitution is less than about 0.18, less than about 0.15, less than about 0.13, or less than about 0.10. In some embodiments, the degree of substitution is greater than about 0.01, greater than about 0.03, greater than about 0.05, or greater than about 0.07. Embodiments of the invention may have any combination of maximum and minimum previously specified.

In some embodiments, $R^7$ is hydrogen.

In some embodiments, the polysaccharide further includes a second substituted hydroxyl group having the formula (IV), where formula (III) and formula (IV) are different, and the substituted hydroxyl group of formula (III) and formula (IV) may be on the same or different monomers. Formula (IV) is $Y-(CR^2R^3)_n-NR^4R^5$, where Y is $-O_1-$ or $-O_1C(O)-$, or $-O_1C(O)NR^1-$, $O_1$ is the oxygen atom of said substituted hydroxyl group, and $R^1$ is hydrogen or $C_1$-$C_4$ alkyl; n=1, 2, 3, or 4; where $R^4$ and $R^5$ are independently hydrogen or $C_1$-$C_4$ alkyl. In some embodiments, formula (IV) is $-O_1-(CH_2CH_2)-NH_2$.

It is advantageous to prepare hydrogels that utilize high percentages (e.g., greater than 80%) of polysaccharides. For example, such hydrogels exhibit improved biocompatibility and biodegradation. However, conventional polysaccharides, when used with crosslinking agents, often do not have favorable gel forming characteristics. Polysaccharides with low degrees of substitution of a crosslinking moiety on a hydroxyl group have been found to form hydrogels with high polysaccharide content. Accordingly, in some embodiments, the present invention include hydrogels and hydrogel-forming compositions having at least about 80% of a polysaccharide, wherein the polysaccharide has at least one monomer having at least one substituted hydroxyl group, wherein the substituted hydroxyl group has the formula (III). No particular maximum or minimum degree of substitution is required, so long as a solid gel can be formed. Hydrogels according to these embodiments are described below.

Crosslinked Compositions

In some embodiments the composition is a crosslinked modified polysaccharide described above. The composition may be crosslinked between polysaccharide molecules, or between polysaccharide molecules and one or more other crosslinkable molecules. Other embodiments include compositions of a crosslinked blend of polysaccharide and a second crosslinkable molecule. In some embodiments, the second crosslinkable molecule is a polymer. As used herein, a "crosslinkable" molecule or polymer is a material bearing at least two reactive groups capable of forming a covalent bond or crosslink with the crosslinkable moiety of the polysaccharide. Examples of reactive groups include, for example, vinyl groups, acrylate groups and, methacrylate groups. Crosslinkable polymers having at least two reactive groups are useable, such as, poly(alkyleneglycol) diacrylate, poly(alkyleneglycol)dimethacrylate. Specific examples include poly(ethylene glycol) diacrylate. Other crosslinkable polymers, both degradable and nondegradable may be used. Examples include hyaluronic acid, chitosan or poly (ester amide) polymers having reactive groups. Reactive groups other than double bonds may also be used, such as thiol containing polymers. Thiol containing polymers may crosslink with double bonds on the polysaccharide, or thiol-containing moieties on the polysaccharide. This chemistry may be useful for non-photocrosslinking where UV irradiation is not desirable.

As used herein, a crosslinkable moiety or reactive group is a chemical substituent capable of reacting with another chemical substituent, forming a covalent bond or crosslink between the two moieties. In general, the crosslinking reaction occurs between different crosslinkable polymers, forming a crosslink between, for example, two different polysaccharide molecules, or between a polysaccharide molecule and another crosslinkable polymer. Crosslinks may also occur within a single polysaccharide.

As described above, when a second crosslinkable molecule is used, there may be a non-saccharide linking moiety between the crosslinked polysaccharides. For example, when the second crosslinkable molecule is poly(ethylene glycol) diacrylate, the linking moiety is a polyethyelene glycol. In some embodiments the crosslinked composition is a hydrogel. In other embodiments, the crosslinked composition is a hydrogel comprising a blend of polysaccharide and poly(ethylene glycol) diacrylate.

As mentioned above, hydrogels according to the invention can be formed by crosslinking through use of, for example, chemical and photochemical means. Photochemical crosslinking can offer some advantages including reduction in the exposure to chemical initiators or other reagents, and greater control over degree of crosslinking by having direct control over exposure to light. In many cases, it is still advantageous to reduce the exposure time to UV radiation. For this reason, certain embodiments include hydrogels and hydrogel forming compositions that form solid hydrogels in a particular period of time. For instance, the compositions may form solid hydrogels in less than about 1 hour, less than about 45 minutes, less than about 30 minutes, or less than about 20 minutes using photoirradiation at 365 nm with a lamp power of about 100 W.

Other embodiments include photocrosslinked compositions of the hydrogel forming compositions described above. In other words, embodiments include a hydrogel formed from the hydrogel-forming compositions described above.

Other embodiments include a hydrogel having at least about 80% of at least one polysaccharide portion and up to about 20% poly(ethylene glycol) diacrylate portions, where the polysaccharide portion is derived from a polysaccharide with at least one monomer having at least one substituted hydroxyl group, and the substituted hydroxyl group has the formula (III). The hydrogel is formed by photocrosslinking. As discussed above, formula (III) has the structure $-O_1-C(O)NR^7-CH_2CH=CH_2$ where $O_1$ is the oxygen atom of said substituted hydroxyl group and $R^7$ is hydrogen or $C_1$-$C_4$ alkyl.

Added Components

The compositions described herein may further include a protein, oligonucleotide, pharmaceutical agent, or cells. In some embodiments, the composition comprises a protein, oligonucleotide, or pharmaceutical agent that is released from the composition over time, when present in an environment, for example an aqueous environment, having a lower concentration of the protein, oligonucleotide, or pharmaceutical agent. "Released from the composition" as used herein, means that the concentration of protein oligonucleotide, or pharmaceutical agent in the crosslinked composition decreases. The aqueous environment may be, for instance, a buffer, such as phosphate buffered saline (PBS) or other buffer. The buffered solution may also include dextranase enzyme or dextranase enzyme may be added. The "aqueous environment" also includes situations where the crosslinked composition is administered to a subject for the purpose of delivering a protein, oligonucleotide, or pharmaceutical agent to the subject. The environment into which the protein, oligonucleotide, or pharmaceutical agent is released can be blood, lymph, tissue, for example an organ tissue, gastric juices, or other environment.

In some embodiments, when a crosslinked composition prepared from a modified polysaccharide, poly(ethylene glycol) diacrylate, and protein is incubated at 37° C. in phosphate buffered saline (PBS), less than 10% of the protein (by weight) is released from the crosslinked composition in the first 24 hours.

In some embodiments, when the crosslinked composition or hydrogel is implanted in a body, the protein, oligonucleotide, pharmaceutical agent, or cells may be released over time. There are two basic release mechanisms, diffusion, and degradation, and combinations of the two may occur. In the diffusion mechanism, a higher degree of swelling will make the diffusion faster, thus causing faster release. A hydrogel with a lower degree of crosslinking will also make diffusion faster. A higher degree of crosslinking can cause dense structures, with less diffusion. The degradation rate is of the hydrogel dominated by the degradation of the polysaccharide. In hydrogels (e.g. Dex-AE/PEGDA), a more degradable polysaccharide component means faster degradation, and therefore faster release. Accordingly, persons skilled in the art will be able to modify the hydrogel structure and the polymer to achieve a desired release profile.

In embodiments further including cells, the cells may be, for example, stem cells. In some embodiments, the cells incorporated into the composition may be sources for vascular growth within the composition when implanted into a body. The stem cells may be matched with the organism in which the composition is being implanted. For example, if implanted into a mouse, the stem cells may be mouse cells. If implanted into a human, the stem cells may be human cells. The stem cells may be matched with the organ or tissue to be treated. For example, stem cells for organs such as skin, brain, heart, lungs, gastrointestinal organs, liver, or kidney or tissues such as muscle or subcutaneous tissue may be used. Where stem cells are used, they may differentiate into vascular tissue or surrounding tissue of interest within the composition after implantation. Other components, such as, for example, NO releasing compounds, that promote vascular differentiation can also be included.

Methods

Hydrogels according to the invention can be used as tissue engineering scaffolds to increase neovascularization, vascular regeneration, or tissue growth or regeneration. As used herein, "increased" neovascularization means that more, longer, or larger new blood vessels grow in the presence of the composition when compared with the absence of the composition. As used herein, "increased" vascular regeneration means that damaged blood vessels, or existing blood vessels grow faster in the presence of the composition when compared with the absence of the composition. As used herein, "increased" tissue growth or regeneration means faster growth or repair of damaged tissues when compared with the absence of the composition. Neovascularization, vascular regeneration or tissue growth may occur around the implanted composition, or in suitable embodiments, such as hydrogels and scaffolds, vascular or tissue in-growth may occur inside the hydrogel or scaffold.

When the combination of growth factors is administered in a composition described above, the growth factors are released over time from the composition, causing increased vascular and/or tissue growth. The composition may be administered subcutaneously (i.e. below the skin) to increase vascular growth or regeneration. In other embodiments, the composition may be implanted at a specific location in the body, inducing vascular or tissue growth for the treatment of, for example, ischemias. Compositions described herein may be used to increase repair, growth, or regeneration of damaged tissues. The compositions may also be used to increase healing of damaged subcutaneous tissues, such as, for example, in burns.

The crosslinked compositions and hydrogels described herein may be administered by any available route for administering hydrogels to a subject. In some embodiments, the composition may be administered to a subject as an uncrosslinked composition, followed by crosslinking in situ. In this way, the hydrogels may be molded to a particular shape, based on the location of administration, for example on a targeted organ. The uncrosslinked composition may be crosslinked before or after administration, externally or internally.

In some embodiments, the composition is crosslinked prior to administration. The crosslinked composition may be formed in a particular shape, for example as ovoid, sphere, disc, sheet or other structure as desired for the site of treatment.

After administration, the growth factors are released from the composition. The rate of release may be steady, i.e. a certain percentage, by weight, over a period of time. In other embodiments, the growth factors may be released at an increasing initial rate after administration, followed by a steady-state release. In other embodiments, the rate of release may decrease over time after administration.

In some embodiments, a certain percentage of the growth factors are released in a given period of time. Embodiments of the invention include methods for sustained release by administering compositions described previously. In some embodiments, the growth factors may be released over about 24 hours or more, about 48 hours or more, or about 72 hours or more.

For example, less than about 10%, by weight, of the growth factors may be released from the crosslinked composition in the first 24 hours. In different embodiments, less than about 30%, less than about 20%, less than about 10%, or less than about 5% by weight may be released over the first 12 hours, 24 hours, or 48 hours. Zero order release, where the additional component is released at a steady state is advantageous in certain circumstances. In other cases, a temporal, stimuli responsive release is desirable. The release profile may be selected based on the desired application.

The release profile may be modified by changing the substituent(s) on the polysaccharide, or by varying the ratio between modified polysaccharide and second crosslinkable compound in the crosslinked composition, by varying the sizes of the polysaccharide or second crosslinking compound, or by changing the degree of substitution on the polysaccharide. Other factors such as pH may also influence the rate of release. The release profile is also influenced by the degradation rate of the crosslinked composition, which will vary from subject to subject.

There are two basic release mechanisms, diffusion, and degradation, and combinations of the two may occur. In the diffusion mechanism, a higher degree of swelling will make the diffusion faster, thus causing faster release. A hydrogel with a laower degree of crosslinking will also make diffusion faster. A higher degree of crosslinking can cause dense structures, with less diffusion. The degradation rate is of the hydrogel dominated by the degradation of the polysaccharide. In hydrogels (e.g. Dex-AE/PEGDA), a more degradable polysaccharide component means faster degradation, and therefore faster release. Accordingly, persons skilled in the art will be able to modify the hydrogel structure and the polymer to achieve a desired release profile.

The vascularization of functional blood vessels is the major limitation in transplanting tissue constructs (Rafii et al., Nat Med, vol. 9, no. 6, pp. 702-12, 2003), and the successful revascularization of ischemic, wounded, and regenerating tissues is essential to restore their functions (Murphy et al., Biomaterials, vol. 21, no. 24, pp. 2521-7, 2000). Optimizing the architecture of biodegradable polymeric scaffolds such as hydrogels described herein to allow fast tissue and vascular ingrowth with the release of angiogenic factors is critical in advancing therapeutic angiogenesis. The present invention includes optimized hydrogel scaffolds for rapid in vivo vascularization that could be used for therapeutic vascular regeneration.

Driven by specific applications, the design of scaffolds takes into consideration such properties as structural characteristics, mechanical strength, and biodegradation. During wound healing, cells infiltrate into and degrade the scaffold, thereby releasing entrapped growth factors (GFs), and with the speed of tissue regeneration, the scaffold is completely absorbed when tissue healing is achieved. The initial cellular infiltration, mostly by macrophages, occurs at the tissue-scaffold interface and is determined by the scaffold structure. The tissue ingrowth rate depends largely on the scaffold structure and degradation rate; large pore size and fast degradation expedite tissue ingrowth (Mikos et al., Biotechnol Bioeng, vol. 42, no. 6, pp. 716-23, 1993). Cell and nutrition transport into the large pore scaffolds occurs relatively easily, even without any measurable degradation. Neither previous results (Sun et al., J Biomed Mater Res Part A, vol. 93A, no. 3, pp. 1080-90, 2010) nor published results with denser crosslinking (Phelps et al., Proc Natl Acad Sci USA, vol. 107, no. 8, pp. 3323-8, 2010; Lee et al., Nature vol. 408, no. 6815, pp. 998-1000, 2000) showed any distinct blood vessel formation within a hydrogel. Reducing the number of crosslinkable groups leads to hydrogels with relatively loose structures, which gave rise to tunable hydrogel scaffolds. In some exemplary embodiments, results demonstrate that the reduction in DS of Dex-AE improved hydrogel properties—for example, increased swelling, release capability, and provides a wider, tunable range of mechanical strength—all consistent with previous findings (Sun et al., J Biomed Mater Res Part A, vol. 93A, no. 3, pp. 1080-90, 2010). Without being bound by theory, the swelling of this type of hydrogel may be predominately determined by its structure (Sun et al., J Biomater Sci-Polym Ed vol. 20, no. 14, pp. 2003-22, 2009; Sun et al., Carbohydr Polym vol. 65, no. 3, pp. 273-87, 2006), and increased swelling may be mainly caused by increased porosity. As diffusion is one of the major release mechanisms from hydrogel scaffolds (Langer, Science, vol. 249, no. 4976, pp. 1527-33, 1990), an increase in porosity may facilitate diffusion and lead to higher and more complete release. Furthermore, pre-loaded GFs are mostly entrapped within the walls of porous networks, and the reduction in crosslinking density may have a direct effect on diffusion capability.

An in vivo study revealed faster tissue ingrowth and hydrogel fragmentation with the increase of Dex-AE content. The immunohistochemical stains indicated cellular infiltration into the gel, primarily by macrophages, followed by neovasculature. Faster tissue ingrowth was believed to be caused by increased porosity (more and larger pores with an interconnected pore structure) and faster degradation. This approach enables a reduction in crosslinking density while increasing degradation by increasing dextran content in the hydrogel (Sun et al., 3 Biomed Mater Res Part A, vol. 93A, no. 3, pp. 1080-90, 2010). Reduced crosslinking can give rise to a highly porous structure, which may promote tissue and vascular ingrowth (Cao et al., Biomaterials, vol. 27, no. 14, pp. 2854-64, 2006). With cellular infiltration, the hydrogel scaffold may be degraded and replaced by host tissues; the degradation would facilitate open porous structures and promote tissue ingrowth.

In examples with the encapsulation of angiogenic GFs, distinct functional vascular structures were observed, including arterioles and venules, within the scaffolds. This is of particular interest for large wounds associated with tissue injury which, unlike small wounds in which capillary proliferation might be sufficient for healing, require a more complex neovascularization.

In exemplary embodiments, the delivery of VEGF promotes tissue ingrowth and functional vascularization. In the examples that follow, five-week-long study first revealed significantly more tissue ingrowth, primarily by macrophages, into the VEGF-encapsulated hydrogel than into blank hydrogel. This result may suggest that VEGF attracts circulating cells into the hydrogel, thus promoting tissue penetration. Phelps et al. also found that matrices lacking VEGF showed less tissue invasion than VEGF-incorporating matrices (Phelps et al., Proc Natl Acad Sci USA, vol. 107, no. 8, pp. 3323-8, 2010). The tissue ingrowth might further expedite scaffold biodegradation, which in return could facilitate further ingrowth. This result was further confirmed by a three-week-long multiple GF delivery study; without the VEGF encapsulation, in which neither the blank hydrogel nor the hydrogel loaded with SDF-1 and IGF showed any significant tissue ingrowth. Although Cohen et al. (Dvir et al., Proc Natl Acad Sci USA vol. 106, no. 35, pp. 14990-5, 2009) demonstrated that a scaffold encapsulated with SDF-1 and IGF promoted prevascularization when implanted onto a rat omentum, these hydrogels revealed neither significant tissue ingrowth nor vascular structures with the encapsulation of SDF-1 and IGF. Overall, these results suggest that VEGF delivery is required to initiate sufficient tissue ingrowth, which eventually leads to functional vascular development within the hydrogel implants.

Vascular engineering seeks to either induce or create functional vascular structures to restore damaged blood vessels or to perfuse local parenchymal cell populations with functional nutrient networks. This can be achieved by controlling and manipulating some of the signaling pathways involved in neovascularization (Sun et al., Regenerative Medicine, vol. 3, no. 3, 435-47, 2009; Hanjaya-Putra et al., Biotechnol Prog, vol. 25, no. 1, pp. 2-9, 2009). Angiogenic growth factors (GFs) are major driving forces of neovascularization, which makes directing these cues therefore critical for the induction of new blood vessels (Banfi et al., Curr Atheroscler Rep vol. 7, no. 3, pp. 227-34, 2005). Thus, local delivery of angiogenic GFs is highly desirable for therapeutic angiogenesis (Richardson et al., Nat Biotech vol. 19, no. 11, pp. 1029-34, 2001). Among these different GFs, vascular endothelial GF (VEGF)—which regulates the migration, survival, proliferation, and differentiation of endothelial cells (ECs) (Fan et al., FASEB J, vol. 22, no. 10, pp. 3571-80 2008; Peattie et al., vol. 25, no. 14, pp. 2789-98, 2004)—plays a key role in new blood vessel formation (Prior et al., J Appl Physiol vol. 97, no. 3, pp. 1119-28, 2004). Insulin=like GF (IGF) increases the overall bioavailability of nitric oxide, which recruits endothelial progenitor cells (EPCs) from the bone marrow (Fleissner et al., Mol Med vol. 14, no. 5-6, pp. 235-7, 2008) and stimulates angiogenesis and neovascularization (Delafontaine et al., Arterioscler Thromb Vase Biol, vol. 24, no. 3, pp. 435-44, 2004). Stromal-cell-derived factor-1 (SDF-1) also increases EPC mobilization and stimulates angiogenesis (Petit et al., Trends Immunol vol. 28, no. 7, pp. 299-307, 2007; Urbich et al., Circ Res, vol. 95, no. 4, pp. 343-53, 2004). Additionally, angiopoietin-1 (Ang-1) induces smooth muscle cell (SMC) recruitment for neovessel stabilization and promotes vessel outgrowth (Chen et al., Arterioscler Thromb Vasc Biol vol. 28, no. 9, pp. 1606-13, 2008). Most clinical and preclinical trials center on delivery of a single GF (Phelps et al., Proc Natl Acad Sci USA, vol. 107, no. 8, pp. 3323-8, 2010); however, as the formation of blood vessels requires a dynamic interplay of multiple signaling cues, the co-release of multiple GFs and the corresponding synergistic effect are more desirable for therapeutic vascular regeneration.

Angiogenesis is modulated by various signaling cues, and the delivery of multiple GFs has the potential for synergistic effects on vascular formation (Asahara et al., Circulation, vol. 92, no. 9, pp. 365-71, 1995). Although VEGF delivery was found to stimulate functional vascularization, this was not observed until five weeks after implantation, implying that VEGF alone has a limited capability to induce larger blood vessels (Phelps et al., Proc Natl Acad Sci USA, vol. 107, no. 8, pp. 3323-8, 2010). Faster and greater vascularization may be possible with the delivery of additional GFs. Results presented herein demonstrate a synergistic effect of angiogenic GFs, when used in conjunction with the delivery of VEGF. In hydrogels according to the invention, for example, the coadministration of VEGF and Ang-1 and of VEGF, IGF, and SDF-1 induces more and larger blood vessels than any individual GF. Additionally, the combination of VEGF, SDF-1, IGF, and Ang-1 led to a dramatic increase in the size and number of arterioles and venules and enhances the progression of neovascularization overall. Controlled delivery of angiogenic GFs by covalent incorporation of thiol-modified heparin in polysaccharide hydrogels (Elia et al., Biomaterials, vol. 31, no. 17, pp. 4630-8, 2010) or by pre-encapsulating factors in microspheres (Richardson et al., Nat Biotech, vol. 19, no. 11, pp. 1029-34, 2001), significantly improved vascularization, but produced little association with the matrix. This might be attributed to the scaffold properties, suggesting a need for modification of hydrogel properties to facilitate rapid vascularization.

Although engineering porous hydrogel scaffolds for vascularization remains a challenge (Keskar et al., J Tissue Eng Regen Med, vol. 3, no. 6, pp. 486-90, 2009), this invention demonstrates that a rapid, efficient, and functional neovascularization can be achieved by manipulating the architecture of dextran hydrogel scaffolds and the release of angiogenic GFs, which may impact a wide range of vascular regenerative therapeutics.

Rapid, efficient, and functional neovascularization was successfully achieved using hydrogels according to the present invention. The hydrogel structure can be prepared by decreasing crosslinking density via reduced degree of substitution of crosslinking groups. This reduction in hydrogel crosslinking density offers a wide range of improved properties that can be readily modified by persons having ordinary skill in the art. With the encapsulation of angiogenic GFs (i.e., VEGF, IGF, SDF-1 and Ang-1), abundant functional blood vessels are formed in vivo. The compositions of the present invention can be useful for therapeutic vascularization and wound healing.

Preparation

The polysaccharides used in compositions according to the invention may be prepared according to methods known in the art. For example, polysacchrides may prepared according to methods described in WO 2010/078036, which is incorporated by reference in its entirety. Other hydrogels are described, for example by Hennick et al. (Adv. Drug Deli. Rev., vol. 54, no. 1, pp. 13-36, 2002) which is also incorporated by reference in its entirety.

For example, an unsubstituted polysaccharide bearing a reactive hydroxyl group may be reacted with a reagent bearing a crosslinkable moiety to produce structure having hydroxyl groups modified to incorporate formula (I). The reagent may react with the free hydroxyl group directly, or the reagent or hydroxyl group may be activated to react with the reagent. Examples of substituents which may react directly with the free hydroxyl group to produce the structure of formula (I) include epoxides, such as glycidyl acrylate and glycidyl methacrylate; anhydrides, such as maleic anhydride, acrylic anhydride, or methacrylic anhydride; isocyanates, such as allyl isocyanate; acyl halides, such as acryloyl chloride, or methacryloyl chloride; alkyl halides such as allyl bromide, or 2-chloroethyl acrylate, or 2-chloroethyl methacrylate. Other reagents may have activatable groups, i.e. moieties that can be activated to react with the free hydroxyl group. Activateable groups include carboxylic acids, hydroxides or amines to form, for example, esters, ethers, carbonates, or carbamate (urethane) linkages.

Polysaccharide having substituted hydroxyl groups with the structure of formula (III) may be prepared, for example, by reacting a polysaccharide with allylisocyanate in the presence of an activator, such as dibutyltin dilaurate (DBTDL). The degree of substitution is controlled by reducing the mole ratio of allylisocyanate to polysaccharide to produce the desired degree of substitution.

A hydroxyl group on the polysaccharide may be substituted to form the substituent of formula (I) first, followed by substituting another hydroxyl group to form the substituent of formula (III), or vice versa. In some cases, both substituents may be formed in the same reaction by adding both reagents to the unsubstituted polysaccharide.

The modified polysaccharide having the substituent of formula (I) or (III) may then be reacted with a reagent to form a substituent of formula (IV) using reagents discussed previously. Substituents of formula (IV) where Z is $NR^5R^6$ may be prepared, for example, by reacting the modified polysaccharide with an amine bearing reagent similar to those described previously having a carboxylic acid. For example, the polysaccharide may be reacted with 2-bromoethylamine hydrobromide to form the substituent having the formula $—O_1—(CH_2CH_2)—NH_2$. Alternatively, a polysaccharide may be reacted with a reagent to form a substituent of formula (IV), and then reacted with a reagent to form a hydroxyl group with the structure of formula (III).

The polysaccharide may be purified, for example, by precipitation, or by chromatography, such as size exclusion chromatography.

Crosslinked compositions may be prepared by crosslinking the modified polysaccharide using any suitable chemistry, based on the crosslinking moiety. In some embodiments, where the crosslinking moiety comprises a double bond, photocrosslinking is used to crosslink the composition. The composition may further include a second crosslinkable molecule or polymer. The second crosslinkable molecule or polymer should have at least two crosslinkable groups capable of forming crosslinks with the crosslinkable moieties of the modified polysaccharide.

Growth factors, including VEGF and additional growth factors may be combined with the modified polysaccharide and other crosslinking compounds prior to crosslinking, or may be diffused into the hydrogel after crosslinking.

Proteins, oligonucleotides, pharmaceutical agents or cells may also be incorporated into the crosslinked composition. In some cases, the protein, oligonucleotide, pharmaceutical agent, or cells are incorporated by soaking the crosslinked compositions in a solution containing the protein, oligonucleotide, pharmaceutical agent, or cells. In other cases, the protein, oligonucleotide, pharmaceutical agent, or cells may be present in a solution or suspension containing uncrosslinked modified polysaccharide, with or without a second crosslinkable molecule. The composition is then crosslinked, for example, by photocrosslinking, to form a crosslinked composition including the protein, oligonucleotide, pharmaceutical agent or cells.

In exemplary embodiments, the modified polysaccharide is a modified dextran molecule, and the second crosslinkable molecule is based on poly(ethylene glycol), for example poly(ethylene glycol) diacrylate (PEGDA).

The preparation of dextran-based hydrogels is illustrated using Dex-AI/PEGDA hydrogels, as shown in FIG. 1, which illustrates the preparation of dextran-based hydrogels through the photocrosslinking of dextran-based precursors and PEGDA, using a long-wave (365 nm) UV lamp. A synthetic polymer precursor can be introduced to have both synthetic and natural polymers in a single resulting hydrogel, thus obtaining further tunable properties. Among synthetic polymer precursors, PEG has been extensively employed for many biomedical applications, due to its unique amphiphilic, biocompatible, but nonbiodegradable properties. Though PEG is not biodegradable, it can be readily excreted from the body via kidney and liver, thereby making it more suitable for biomedical applications. In addition, PEG has been employed to improve biocompatibility (Zhang et al., *Biomaterials*, 2002, vol. 23, p. 2641-2648), to increase bioactivity (Muslim et al., *Carbohydr. Polym.*, 2001, vol. 46. p. 323-330), and to reduce immunogenicity (Hu et al., *Int. J. Biochem. Cell. Biol.*, 2002, vol. 34, p. 396-402).

Including a synthetic polymer, such as poly(ethylene glycol) in the crosslinked composition can provide the capability to further tune the properties of the resulting hydrogel. Tunable properties include mechanical properties, such as the swelling and modulus of the hydrogel. Other properties influenced by the type of synthetic polymer include crosslinking density and the release profile of any incorporated protein, oligonucleotide or pharmaceutical agent.

Properties of the crosslinked composition may be varied by varying the components of the composition, using a different modified polysaccharide, or changing the degree of substitution of one or more substituents on the modified polysaccharide. Other properties may be adjusted by varying the size of the polysaccharide, or the size of the second crosslinkable compound or polymer.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Materials

Dextran (Dex, MW 70000) and allyl isocyanate (AI) were purchased from Sigma Chemical Co. (St. Louis, Mo.). Dextran was dried in an oven for 30 minutes at 60° C. before reaction. Dimethyl sulfoxide (DMSO), dibutyltin dilaurate (DBTDL), 2-bromoethylamine hydrobromide (BEAHB), triethylamine, acryloyl chloride, polyethylene glycol (PEG) (MW 4,000), and other chemicals were purchased from Aldrich Chemical Co. (Milwaukee, Wis.) and used as received. The photoinitiator 2-hydroxy-1-[4-(hydroxyethoxy)phenyl]-2-methyl-1-propanone was obtained from Ciba Specialty Chemicals Corp. (Tarrytown, N.Y.). Human $VEGF_{165}$ was purchased from Pierce Biotechnology (Rockford, Ill.).

Statistics

All measurements of hydrogel properties, including swelling, mechanical strength, release, and in vivo vascularization were performed on duplicate samples, with duplicate readings for each data point. Mechanical tests were done on triplicate samples, with triplicate readings for each data point. Bonferroni post tests and parametric two-way ANOVA tests were performed where appropriate (GraphPad Prism 4.02). Significance levels were determined using post tests between Dex-AI and each of its modifications and were set at: *$p<0.05$, $p<0.01$, and *$p<0.001$. All graphical data is reported.

Synthesis of Dextran Macromers

The synthesis of dextran macromers involved two steps, as shown in Scheme 1, for exemplary modified polysaccharide. Additional modified polysaccharides can be prepared in a similar manner.

SCHEME 1

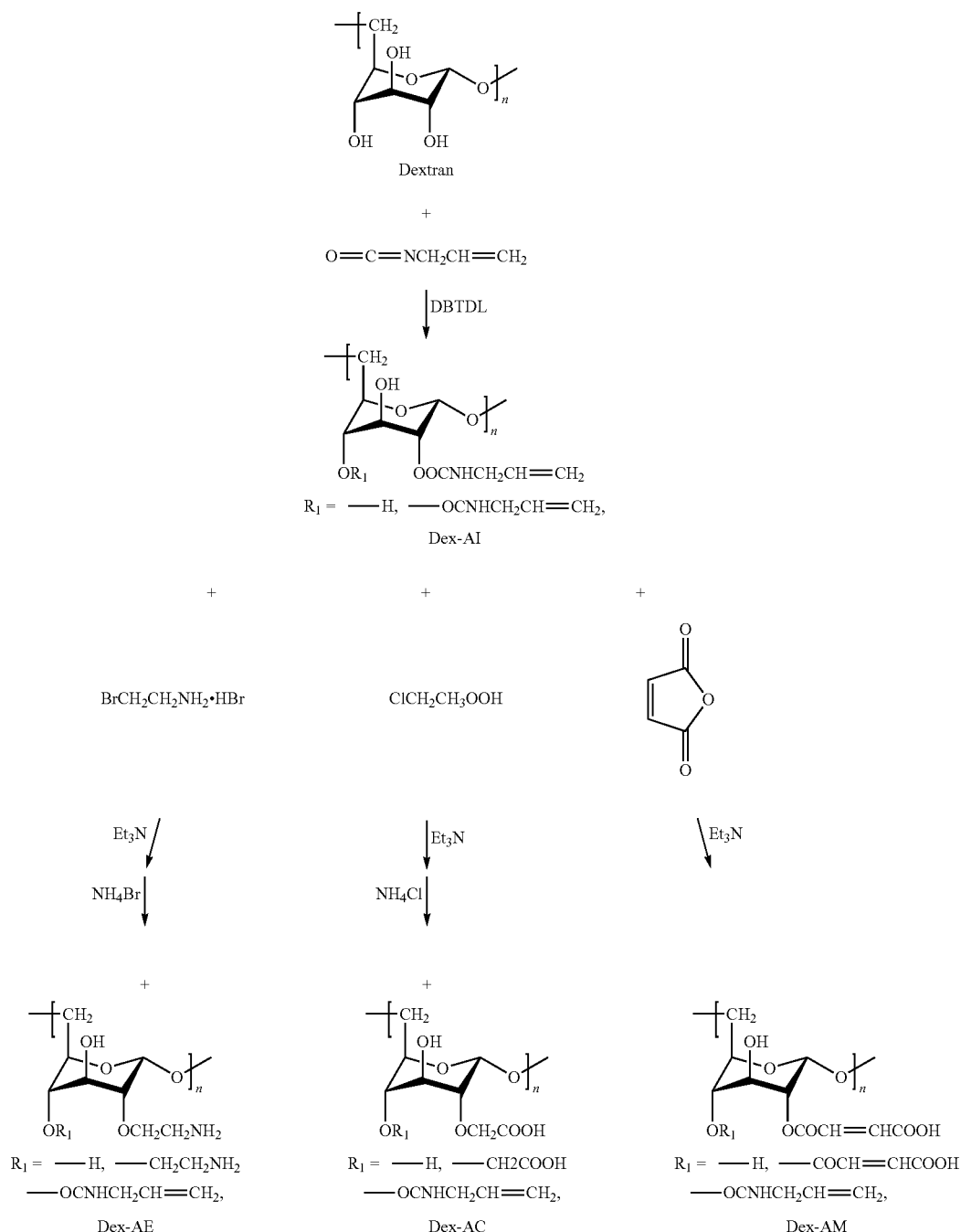

The first step was the incorporation of AI into dextran (to form Dex-AI), followed by further coupling of Dex-AI with BEAHB (to form Dex-AE), AC (to form Dex-AC), and AM (to form Dex-AM). Dex-AI was synthesized and characterized according to published methods Zhang et al., "Synthesis and characterization of Biodegradable Hydrophobic-Hydrophilic Hydrogel Networks with a Controlled Swelling Property," J. Polym. Sci. Polym. Chem., 2000, vol. 38, pp. 2392-2404). Briefly, AI was grafted onto dextran in the presence of DBTDL catalyst. Predried dextran (e.g., 3 g) was first dissolved in anhydrous DMSO under dry nitrogen gas. DBTDL catalyst (1.01 mL) was then injected into the solution, and AI (1.64 mL) was added dropwise to the above solution. The reaction was carried out for five hours at 30° C. The resulting polymer was precipitated in cold excess isopropanol. The product was further purified by dissolution and precipitation in DMSO and isopropanol, respectively. This resulting Dex-AI was then dialysized (molecular weight cut off [MWCO]: 1000 Da) against distilled water for three days, lyophilized for an additional three days, and stored at 4° C. in the dark for further use.

Three different molecules were introduced into Dex-AI. In the preparation of Dex-AE, Dex-AC and Dex-AM, Dex-AI reacted with BEAHB, AC, and AM, respectively. For example, Dex-AC was synthesized in the presence of triethylamine. Predried Dex-AI (3.0 g) was dissolved in anhydrous DMSO under a nitrogen atmosphere. Triethylamine (2.6 ml) was then injected into the above solution. Meanwhile, AC (1.8 g) was dissolved in anhydrous DMSO and then added dropwise to the above solution. This reaction solution was stirred for five hours at 30° C. The resulting Dex-AC polymer was obtained by precipitating into cold isopropyl alcohol. The product was further purified at least three times by dissolution and precipitation with DMSO and cold isopropyl alcohol, respectively. The resulting Dex-AC was dialysized (MWCO: 1000 Da) against distilled water for three days and lyophilized for an additional three days. Dex-AE and Dex-AM were prepared similarly. Dex-AE was also prepared by Sun et al. (*Carbohyd. Polym.* 2006, vol. 65, pp. 273-287).

Results

Different functional groups were introduce by reaction dextran (70 KDa) with a compound having crosslinkable moieties, for example AI, AC, AM, and BEAHB (to form the AE functional group), in two basic steps: the incorporation of AI, followed by the incorporation of amine (Dex-AE) or carboxylic acid (Dex-AC and Dex-AM) moieties. Scheme 1 summarizes this synthesis strategy. Dextran was reacted with AI (Dex-AI) in the presence of dibutyltin dilaurate (DBTDL) catalyst. Unreacted hydroxyl groups in the Dex-AI allowed the reaction with 2-bromoethylamine hydrobromide (BEAHB), chloroacetic acid (AC), and maleic anhydride (AM) to form Dex-AE, Dex-AC and Dex-AM, respectively.

Synthesis of Dextran-Allyl Isocyanate-Ethylamine (Dex-AE)

Dex-AE was synthesized using an improved version of previously published procedures (Sun et al., Carbohydrate Polymers, vol. 65, pp. 273, 2006; Sun et al., Journal of Biomedical Materials Research, Part A, vol. 93A, p. 1080, 2010; Sun et al., Biomaterials, vol. 32, p. 95, 2011). In brief, dry dextran (e.g., 3.0 g) was dissolved in anhydrous DMSO (30 ml) under dry nitrogen gas. DBTDL catalyst (0.1 ml) was injected into the solution dropwise, and AI (0.16 ml) was then added dropwise. The reaction mixture was stirred at room temperature (35° C.) for six hours. The resulting polymer was precipitated in cold excess isopropanol. The product was further purified by dissolution and precipitation in DMSO and isopropanol, respectively.

To synthesize Dex-AE, Dex-AI was further reacted with BEAHB in the presence of triethylamine. Dry Dex-AI (2.0 g) was dissolved in anhydrous DMSO (24 ml) under dry nitrogen gas. Triethylamine (11.2 ml) was injected into this solution. BEAHB (3.75 g) was dissolved in DMSO (10 ml) and then added to the above solution dropwise. This reaction solution was stirred at 50° C. for six hours and then filtered to remove precipitated $Et_3NHBr$. The resulting Dex-AE polymer was obtained by precipitating the filtered solution into cold excess isopropyl alcohol. The product was further purified at least three times by dissolution and precipitation in DMSO and cold excess isopropyl alcohol, respectively. The final product was dried at room temperature under vacuum overnight before further use. The resulting Dex-AE was dialyzed (MWCO: 1000 Da) against distilled water for seven days and lyophilized for an additional three days.

Synthesis of PEG Diacrylate (PEGDA)

PEGDA was synthesized according to previously described methods (Sun et al., J Biomed Mater Res Part A, vol. 93A, no. 3, pp. 1080-90, 2010; Sun J Biomater Sci-Polym Ed, vol. 20, no. 14, pp. 2003-22, 2009; Sun et al. Carbohydr Polym, vol. 65, no. 3, pp. 273-87, 2006). Briefly, predried PEG (8.0 g) was dissolved in anhydrous benzene under a nitrogen atmosphere at 40° C. and then cooled to room temperature. Triethylamine (1.19 mL) and acryloyl chloride (0.81 mL) were subsequently added. The reaction mixture was stirred for two hours at room temperature. The resulting polymer solution was filtered and precipitated in hexane. It was further purified three times by dissolution and precipitation with benzene and hexane, respectively. The PEGDA was then dialyzed (MWCO: 1000 Da) against distilled water for four days and then lyophilized for three days.

Example 1—Preparation of Dex-AE/PEGDA Hydrogel

To explore the effect of different derivatives on hydrogel properties, three different ratios of Dex/PEGDA: low (20/80), medium (40/60), and high (60/40) were examined. The preparation is illustrated using Dex-AI/PEGDA in FIG. 1. Dex-AE and PEGDA were dissolved at different ratios in phosphate buffered saline (PBS) containing 0.1 percent (w/w) 2-methyl-1-[4-(hydroxyethoxy)phenyl]-2-methyl-1-propanone (Irgacure 2959, I2959, Ciba). The mixture was pipetted into a sterile mold (80 μL volume per well) to obtain discs measuring 4 mm in diameter×2 mm thick and photopolymerized (approximately 10 mW/cm$^2$ of UV light for ten minutes; Blak-Ray, UVP, Upland, Calif.). The resulting hydrogels were washed in distilled water for 24 hours to remove unreacted precursors before further characterization.

Swelling Study of Dex/PEGDA Hydrogels

The swelling ratio of dextran-based hydrogels was gravimetrically determined. Predried hydrogel specimens were immersed in distilled water at room temperature. The swollen hydrogels were removed from water at predetermined intervals and weighed after wiping off excess water from the surface with a wet filter paper. The swelling ratio was then calculated according to the following formula:

$$\text{Swelling ratio} = ((W_{s,t} - W_d)/W_d) \times 100\% \quad (1)$$

where $W_d$ is the weight of dry hydrogels, and $W_{s,t}$ is the weight of swollen hydrogels at time t. The hydrogels were assumed to reach a state of swelling equilibrium when there was no difference in swelling ratio between two adjacent intervals.

Figure 2A:
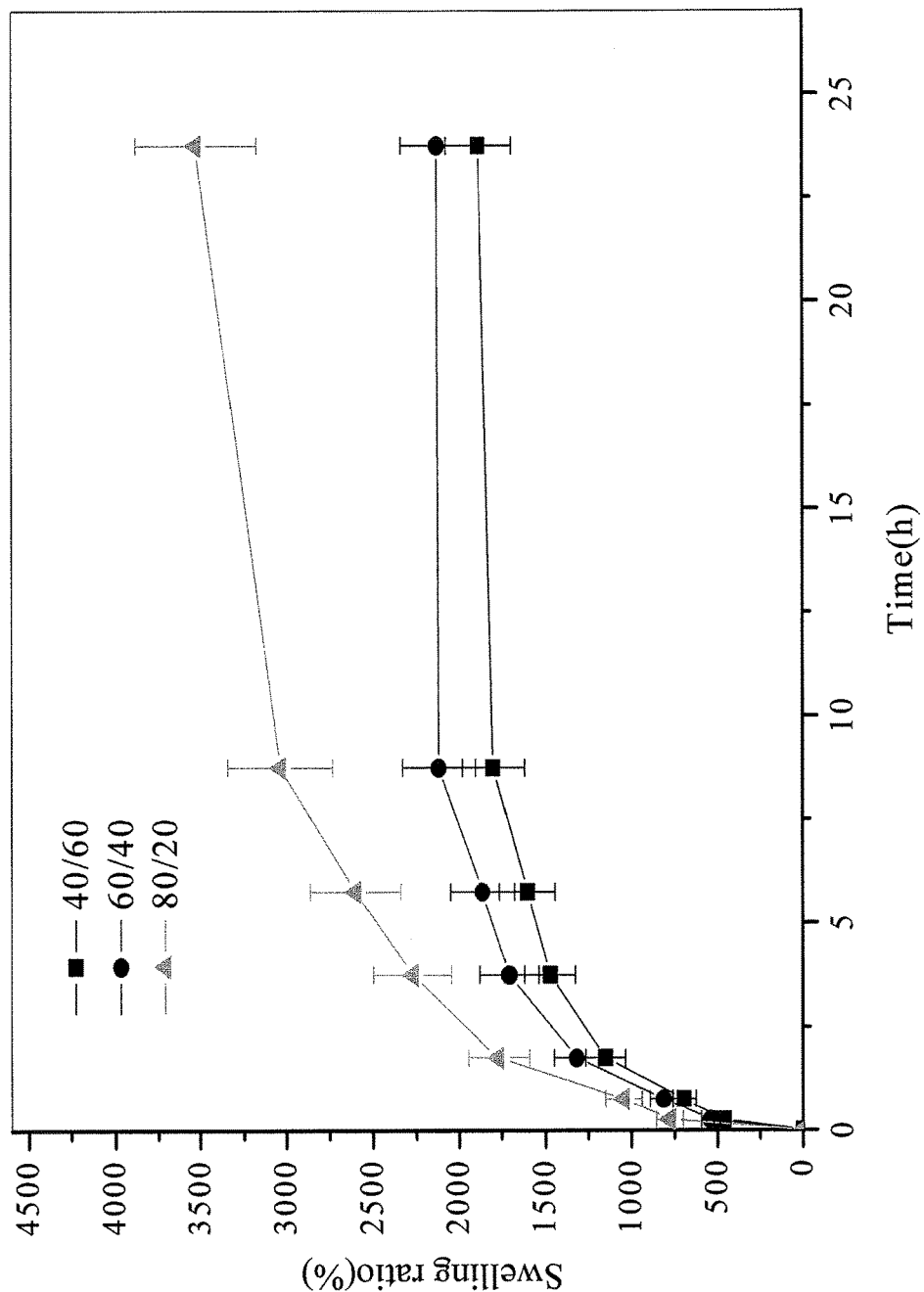
FIG. 2 shows properties of dextran hydrogels. Hydrogels prepared from three different feed ratios of Dex-AE and PEGDA (40/60, 60/40, and 80/20) were examined for: swelling capability (FIG. 2A); mechanical strength (FIG. 2B); and cumulative release of VEGF (FIG. 2C).

The swelling of all hydrogels reached equilibrium at around ten hours, while significant differences in swelling volumes were observed as dextran content increased (FIG. 2A). Maximum swelling volume increased with increasing dextran content (FIG. 2A). Two-way ANOVA analysis revealed that swelling progress over time depended significantly on dextran backbone modification as dextran content increased in Dex-AI/PEGDA, Dex-AM/PEGDA and Dex-AC/PEGDA hydrogels (p<0.001).

Mechanical Study of Dex/PEGDA Hydrogels

The mechanical properties of the hydrogel samples (n=3) were determined using a Q800 Dynamic Mechanical Analyzer (TA Instruments, New Castle, Del.) in unconfined submersion compression mode. Briefly, the diameter of each swollen hydrogel disk was determined using a digital caliper, and the sample was immersed in a PBS bath between unconfined parallel compression platens. Hydrogel samples were compressed at a rate of 10 percent of thickness/min until failure or until they reached 60 percent of their initial thickness. The modulus was then calculated as the ratio of the stress-strain curve at low strain (<25 percent strain), i.e., the linear portion of the curve.

Figure 2B:
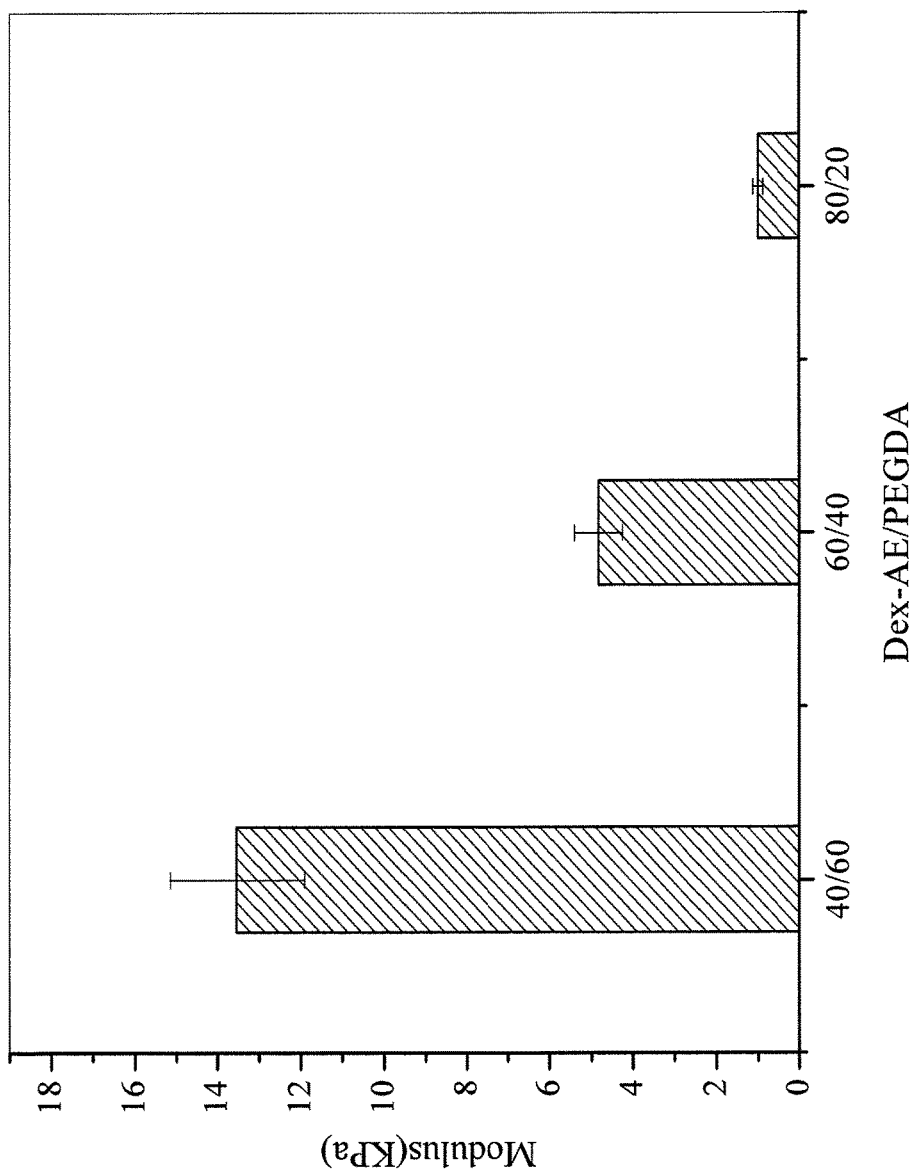

The modulus of the Dex/PEGDA hydrogels decreased with an increase in the Dex/PEGDA ratios (FIG. 2B). Hydrogels at 20/80 Dex/PEGDA ratios were found to have a higher modulus. However, when the dextran macromer in the hydrogel component increased to 60 percent, a dramatic drop in the modulus of Dex-AE/PEGDA and Dex-AM/PEGDA was observed. For example, increasing Dex-AI content in the hydrogel from 20 to 40 percent and then to 60 percent resulted in modulus reduction of 23.6 percent and 48.3 percent, respectively, while modulus reductions of 54.1 percent and 87.7 percent were observed with increased Dex-AE content in the hydrogels.

VEGF$_{165}$ Release Studies

Hydrogel samples were prepared as described above, except that VEGF$_{165}$ (Pierce Biotechnology) was mixed with macromer (1 µg/100 µL) in the mold prior to photopolymerization, resulting in a final VEGF concentration of 20 ng per 1 mg of dry gel. The same amount of Ang-1, IGF, and SDF-1 was loaded for in vivo studies as described below. The solution was then UV-irradiated for ten minutes to allow the gel to form. The gels were carefully removed from the mold, immersed in 2.0 ml of PBS, and incubated at 37° C. At the same time, an equivalent amount of VEGF was incubated in a separated vial and its bioactivity was tested at the same predetermined intervals as the release test. At predetermined intervals, 400 µl of the PBS solution was collected and added 400 µl of blank PBS solution back into the immersion medium to maintain the total solution volume at 2.0 ml. The samples were stored at −80° C. before an ELISA (Pierce Biotechnology) analysis was performed according to the manufacturer's instructions. Briefly, VEGF$_{165}$ in the ELISA kit's standards and samples were captured on the anti-human VEGF$_{165}$ antibody-coated microplate. After removing unbound proteins, biotinylated antibody reagent was added to bind to the secondary site on VEGF$_{165}$. Then, to produce a colorimetric signal, streptavidin-horseradish peroxidase was added to bind to tetramethylbenzidine. Standards were prepared according to the manufacturer's instructions. Plate washing was performed three times between each step to remove any excess reagents. The colorimetric signal was detected using a UV microplate spectrophotometer (SpectraMax Plus, Molecular Devices, Sunnyvale, Calif.) at absorbance wavelengths of 450 and 550 nm. The standard curve was interpolated to determine the amount of VEGF$_{165}$ at each predetermined time point. Results are presented in terms of cumulative release as a function of time:

$$\text{Cumulative release (\%)} = \left(\sum_{t=0}^{t=t} M_t/M_\infty\right) \times 100 \quad (8)$$

where $\sum_{t=0}^{t=t} M_t$ is the cumulative amount of released VEGF from the hydrogel at time t, and $M_\infty$ is the initial amount of loaded VEGF in the hydrogel.

To further assess the in vivo VEGF release from the hydrogel, subcutaneous transplantation (as described above) was performed for a period of up to five weeks.

Example 2—In Vivo Vascularization of Dex-AE/PEGDA Hydrogels

Dex-AE/PEGDA hydrogels were prepared in the shape of a disc (2 mm thick×4 mm diameter) under sterile conditions. Female Lewis rats (Charles River Laboratories, Wilmington, Mass.) weighing 200 to 250 g were housed separately and given access to water and food ad libitum. The animals were cared for according to the approved protocols of the Committee on Animal Care of the Johns Hopkins University, in conformity with the NIH guidelines for the care and use of laboratory animals (NIH publication #85-23, revised 1985). The animals were anaesthetized using continuous 2 percent isoflurane/O$_2$ inhalation. Two sample implantations per time point per rat were performed. Three small midline incisions were made on the dorsum of the rat, and the implants were introduced in lateral subcutaneous pockets created by blunt dissection. Both animals remained in good general health throughout the study, as assessed by their weight gain. At each predetermined time point. (one and three weeks), rats were sacrificed, and the implanted scaffolds were removed en bloc with the surrounding tissue (approximately 10×10 mm). The samples were fixed and processed for histology as described below.

Histology

Dex-AE/PEGDA hydrogel explants were fixed with Accustain® formalin free fixative (Sigma-Aldrich, St. Louis, Mo.) for 24 hours, dehydrated in graded ethanol (70 to 100 percent), embedded in paraffin, serially sectioned using a microtome (5 µm), and stained with either hematoxylin and eosin (H&E) or immunohistochemistry for CD31, ED1, α-SMA and CD3.

Image Analysis

Macrophage response and hydrogel degradation were analyzed through a blind trial. Briefly, multiple ED1 stained images (n=7) were taken from each sample condition. Images were then randomly colligated and given independently to two observers not associated with the study. Each observer ranked the images from 1 to 4, based on cellular ingrowth and gel fragmentation; the rankings signified: 1, a thin layer of macrophages (about 5-10 µm) penetrated the hydrogel, making a smooth contact surface with the hydrogel; 2, a thicker layer of macrophage penetration (<100 µm) with some fractures into the gel; 3, macrophage coverage was greater than 100 µm with more distinct gel degradation; and 4, macrophage covered the whole gel and the gel was completely fragmented. The scoring was then summed, and the average calculated for each experimental condition. Tissue ingrowth was quantified from digital images of H&E-stained tissue sections using ImageJ (NIH software). The tissue ingrowth within the hydrogels was estimated from the fraction area. A minimum of six individual images for each hydrogel condition were analyzed by statistical analysis using GraphPad Prism 4.02 (GraphPad Software Inc., La Jolla, Calif.). Blood vessel number and size were counted, measured, and normalized to tissue area. A minimum of six images were analyzed for each hydrogel, and counted, measured, and normalized the blood vessels accordingly. All statistical analyses were carried out using GraphPad Prism.

Example 3

One major issue of other dextran hydrogels are slow degradation and less tissue ingrowth. The discovery that hydrogels having too much crosslinking density retard the degradation and tissue penetration, may explain this problem. A second problem is the limit on the amount of dextran that can be used to form a stable hydrogel, limiting the degradation rate and extent. Previously, stable hydrogels were formed only at Dextran/PEGDA ratios between 70/30 and 0/100 (Sun et al., *Carbohydrate Polymers*, 2006; vol.

65). In this study, newly prepared hydrogels were examined having Dex-AE and PEGDA at three different ratios of Dex-AE/PEGDA: low (40/60), medium (60/40), and high (80/20). The new Dex-AE have much lower degree of substitution of allyl isocyanate groups, which incorporate double bonds and provide the crosslinking sites. Differences in physical and biological properties of the hydrogels are found, including swelling, mechanics, vascular endothelial growth factor release, and in vivo vascular formation.

Synthesis of Dextran Macromers Having Low Degree of Substitution

Dry dextran (e.g., 3.0 g) was dissolved in anhydrous DMSO (30 ml) under dry nitrogen gas. DBTDL catalyst (0.1 ml) was injected into the solution dropwise, and AI (0.16 ml) was then added dropwise. The reaction mixture was stirred at 30° C. for 6 hours. The resulting polymer was precipitated in cold excess isopropanol. The product was further purified by dissolution and precipitation in DMSO and isopropanol, respectively. The degree of substitution (DS, the number of substitution groups per anhydroglucose unit) of AI obtained under this condition is 0.09, as determined by NMR.

To synthesize Dex-AE, Dex-AI prepared above was further reacted with 2-bromoethylamine hydrobromide (BEAHB) in the presence of triethylamine. Dry Dex-AI (2.0 g) was dissolved in anhydrous DMSO (24 ml) under dry nitrogen gas. Triethylamine (11.2 ml) was injected into the above solution. BEAHB (3.75 g) was dissolved in DMSO (10 ml) and then added to the above solution dropwise. This reaction solution was stirred at 50° C. for 6 hours. The reaction mixture was then filtered to remove precipitated $Et_3NH_4Br$. The resulting Dex-AE polymer was obtained by precipitating the filtered solution into excess cold isopropyl alcohol. The product was further purified at least 3 times by dissolution and precipitation in DMSO and cold isopropyl alcohol, respectively. The final product was dried at room temperature under vacuum overnight before further use. The resulting Dex-AE was dialysized (MWCO: 1000 Da) against distilled water for seven days and lyophilized for an additional three days.

Preparation of Dex-AE/PEGDA Hydrogel

Dex-AE and PEGDA were dissolved at different ratios (as described above) in phosphate buffered saline (PBS) containing 0.1% (w/w) 2-methyl-1-[4-(hydroxyethoxy)phenyl]-2-methyl-1-propanone (Irgacure 2959, I2959, Ciba). The mixture was pipetted into a sterile mold (80 μL volume per well, to obtain discs measuring 4 mm in diameter×2 mm thick), and photopolymerized (approximately 10 mW/$cm^2$ of UV light for ten minutes; BlakRay). The resulting hydrogels were washed in distilled water for 24 hours to remove unreacted precursors before further characterization.

Optimized DS Improves Desired Hydrogel Properties

Previous studies demonstrated that incorporating different functional groups into dextran affects both the physical and biological properties of dextran-based hydrogels. Hydrogel prepared from Dex-AE and PEGDA showed the desired physical properties, with enhanced biocompatibility and integration with host tissue (Sun, J Biomed Mater Res Part A, vol. 93A, no. 3, pp. 1080-90, 2010). Here, vascularization kinetics of Dex-AE/PEGDA hydrogels were improved to enable a more rapid integration with the host circulation after implantation. Reduced crosslinking density may facilitate scaffold-tissue interactions and promote rapid host tissue ingrowth and vascularization of the scaffold during the wound healing process.

The DS of AI into dextran is the number of substitution groups per anhydroglucose unit. Therefore, the DS of AI would determine the number of available C=C double bonds for photo-crosslinking, which in return would affect crosslinking density. Dex-AE was synthesized with a low crosslinking density that would still permit hydrogel formation. As illustrated in FIG. 1, the hydrogel is made of numerous crosslinked networks, and the reduction in the DS of crosslinkable group leads to a more porous structure.

To determine the effect of the DS, Dex-AE was synthesized with the DS ranging from 0.04 to 0.35. With a DS of 0.09, approximately 25% of the original Dex-AE, optimally generated Dex-AE hydrogels with only 20% PEGDA (Table 1).

TABLE 1

|  | 0.05X | 0.1X | 0.25X | 0.5X | 1X | 1X | 1X |
|---|---|---|---|---|---|---|---|
| Reaction Temp.(° C.) | 30 | 30 | 30 | 30 | 30 | $25^{a,b}$ | $45^b$ |
| DS | <0.05 | 0.09 |  |  | 0.35 | 0.25 | 0.77 |
| 80/20 | $-^1$ | + | ± | ± | $-^2$ | $-^3$ | $-^4$ |
| 100/0 | − | ± | − | − | − | − | − |

Note:
The precursor concentration was 0.1 g/mL;
+ stands for gel can be formed within 10 min,
− stands for gels cannot form,
± stands for gel can form, but are not as solid.
$^1$at 80/20, the precursor did not form hydrogels within 10 minutes, but forms in 20-30 minutes.
$^{2,3,4}$at 80/20, the precursor did not form hydrogels even at longer time.

DS=0.09 was chosen for further study. Three hydrogels were examined with varying compositions of Dex-AE and PEGDA: 40% Dex-AE/60% PEGDA (40/60) and 60% Dex-AE/40% PEGDA (60/40) both of which were also studied earlier with the DS=0.35 Dex-AE (Sun et al., J Biomed Mater Res Part A, vol. 93A, no. 3, pp. 1080-90, 2010), allowing a direct comparison of hydrogel properties—and 80% Dex-AE/20% PEGDA (80/20), which was formed only with this Dex-AE (Table 1).

Swelling Study of Dex/PEGDA Hydrogels

The water retention capability was studied by studying the swelling ratios of the different Dex-AE/PEGDA hydrogels. As shown in FIG. 2A, the hydrogels reached an equilibrium swelling state within approximately ten hours, except for the hydrogel at the feeding ratio of 80/20, which exhibited a slight increase in swelling ratio. With a larger Dex-AE component, faster and higher swelling capacity was observed; however, these hydrogels showed much higher swelling ratios than those previously. For example, the 60/40 composition of Dex-AE/PEGDA swelled 2100%, while its previous swelling ratio was 1300% (Sun et al., J Biomed Mater Res Part A, vol. 93A, no. 3, pp. 1080-90, 2010). This increased swelling ratio may be attributed to the relatively loose structure of the newly synthesized dextran hydrogels, which results from the reduced number of crosslinking sites and, consequently, its lower crosslinking density.

Mechanical Study of Dex/PEGDA Hydrogels

Appropriate mechanical strength was determined for implantable 3D hydrogel scaffolds. These hydrogels impart tailored control over the mechanical strength of the scaffolds. FIG. 2B shows that increasing the Dex-AE content in the hydrogel decreased its mechanical strength, confirming previous results (Sun et al., J Biomed Mater Res Part A, vol. 93A, no. 3, pp. 1080-90, 2010). Furthermore, the 40/60 and 60/40 compositions had hydrogel moduli similar to previous results (13-15 KPa and 4-5 KPa, respectively), suggesting that the decrease in the number of double bonds in the Dex-AE hydrogel did not affect the hydrogel structure significantly. This result also suggests that only a small amount of photocrosslinking is necessary to provide mechanical strength. A higher degree of crosslinking usually gives rise to brittle structures, which compromise the mechanical properties of the hydrogel (Gong et al., Adv Mater, vol. 15, no. 14, pp. 1155-8, 2003).

GF Release

Figure 2C:
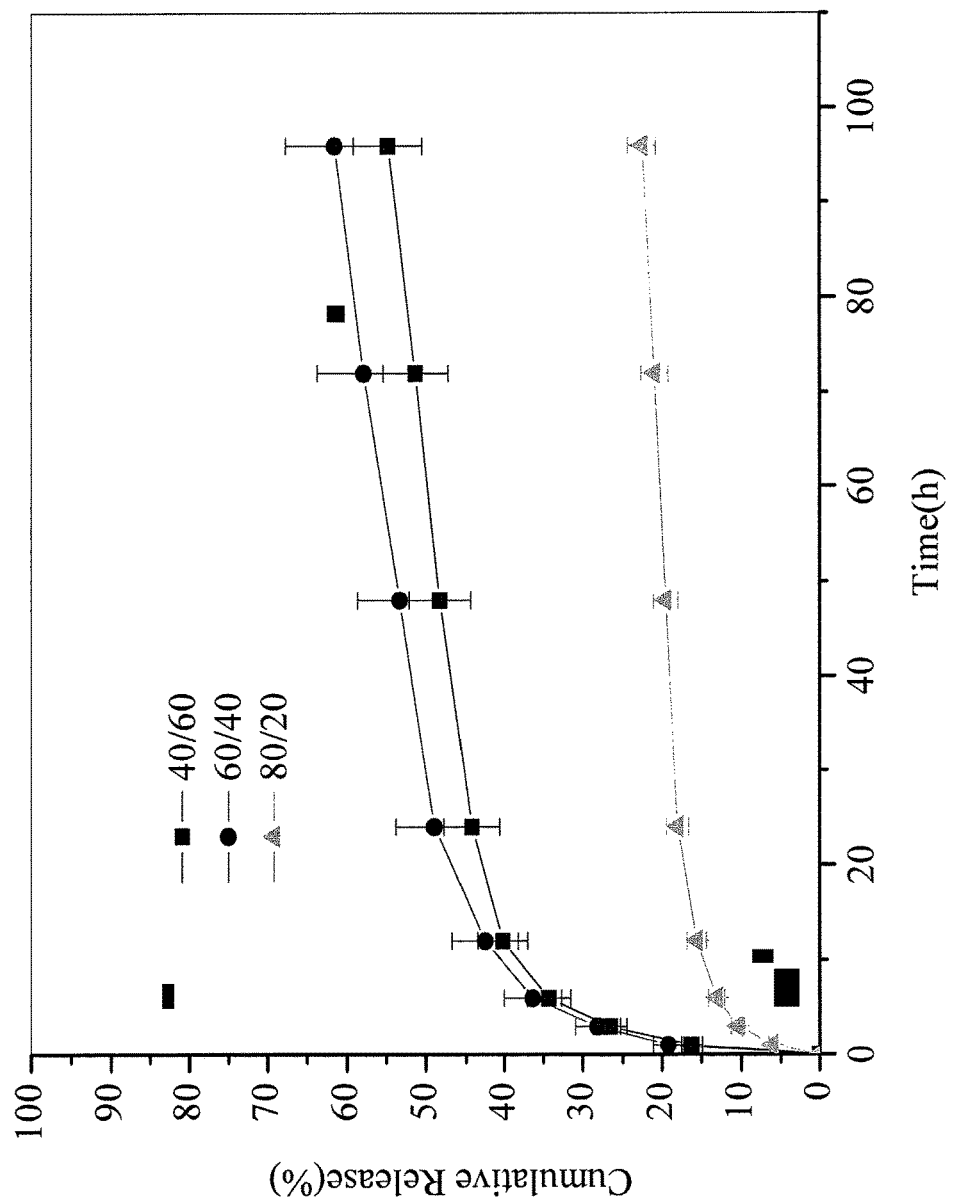

GFs provide important signaling information for vasculogenesis. Here, ELISA was used to determine the bioactive VEGF release from the hydrogels over time. FIG. 2C shows that 40/60 and 60/40 compositions produced a burst release of VEGF, with about 35% of VEGF released during the first 10 hours, and over 50% released within 96 hours. This was greater than previously reported, which indicated that 18% of VEGF was released within 96 hours (Sun et al., J Biomed Mater Res Part A, vol. 93A, no. 3, pp. 1080-90, 2010). However, much less burst release was detected in the hydrogel at the ratio of 80/20, where the release reached approximately 20% within 96 hours.

Release from hydrogels is predominantly driven by diffusion, degradation, or both. Generally, prior to degradation, diffusion is the primary release mechanism; thus, release is dominated by swelling. As discussed above, the hydrogels swelled much more than previous hydrogels, contributing to the greater GF release. Surprisingly, the VEGF release from the 80/20 hydrogel was much less than that from the other two hydrogels. This reduced release might be attributed to the presence of amine groups. An increased proportion of Dex-AE in the hydrogel feeding ratios increased the number of amine groups, which is known to increase interactions with protein-based compounds (Sun et al., J Biomater Sci-Polym Ed vol. 20, no. 14, pp. 2003-22, 2009), thereby enhancing the interactions between the scaffold and the VEGF, which would reduce the burst release and prolong the VEGF release period.

Example 4—Increase in Dex-AE/PEGDA Ratio Enhances Tissue Ingrowth

Figure 3:
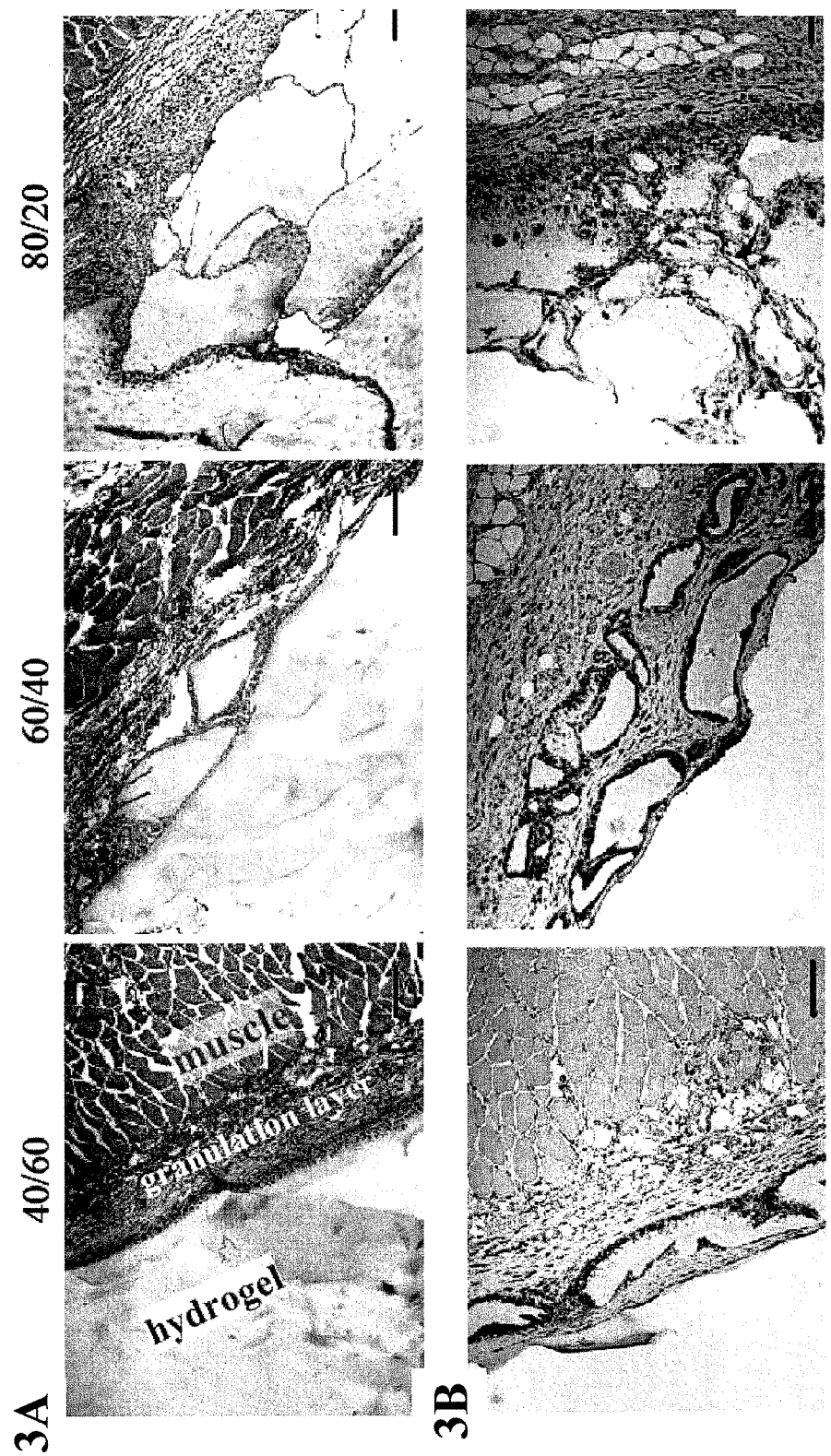
FIG. 3 shows that increasing Dex-AE/PEGDA ratio enhances tissue ingrowth. Dextran hydrogels at three feeding ratios were examined one week after subcutaneous transplantation.

Vascularization is an important therapeutic effect: it provides enhanced nutrition transport and maintains the engineered tissue. To identify the most appropriate hydrogel composition for promoting vascularization, each type of hydrogel was implanted subcutaneously in rats. Within seven days, increased penetration of cellular strands into the hydrogels was observed with larger Dex-AE/PEGDA ratios (FIG. 3A). Analysis of the penetration depth of macrophages and hydrogel degradation revealed that, within seven days, a significantly deeper macrophage layer and greater gel fragmentation were observed in 80/20 hydrogels, compared to limited and nonpenetration in 60/40 and 40/60 hydrogels, respectively, as shown in Table 2 below. This trend continued throughout the transplantation period (FIG. 3B), confirming that the 80/20 hydrogel is more suitable for further study as a vascular growth construct.

TABLE 2

Blind study of depth of macrophage penetration

| | 40/60 | 60/40 | 80/20 |
|---|---|---|---|
| W1 | 1.42 ± 0.20 | 2.00 ± 0.55 | 2.83 ± 0.99** |
| W3 | 2.42 ± 0.44 | 2.75 ± 0.44 | 2.97 ± 0.63 |
| W5 | 2.79 ± 0.68 | 2.83 ± 0.41 | 3.35 ± 0.53 |

Significance levels (against 40/60) were set at:
*$p < 0.05$,
**$p < 0.01$, and
***$p < 0.001$.
Values shown are means ± SD.

Index:
1—A thin layer of macrophages (about 5-10 um) penetrated the hydrogel, with smooth contact surface with hydrogel.
2—A thicker layer of macrophages penetration (<100 um) with some fractures into the gel.
3—Macrophage coverage is greater than 100 um with more distinct gel degradation.
4—Macrophage covers the whole gel and the gel is completely fragmented.

VEGF Delivery Expedites Functional Neovascularization

Figure 4:
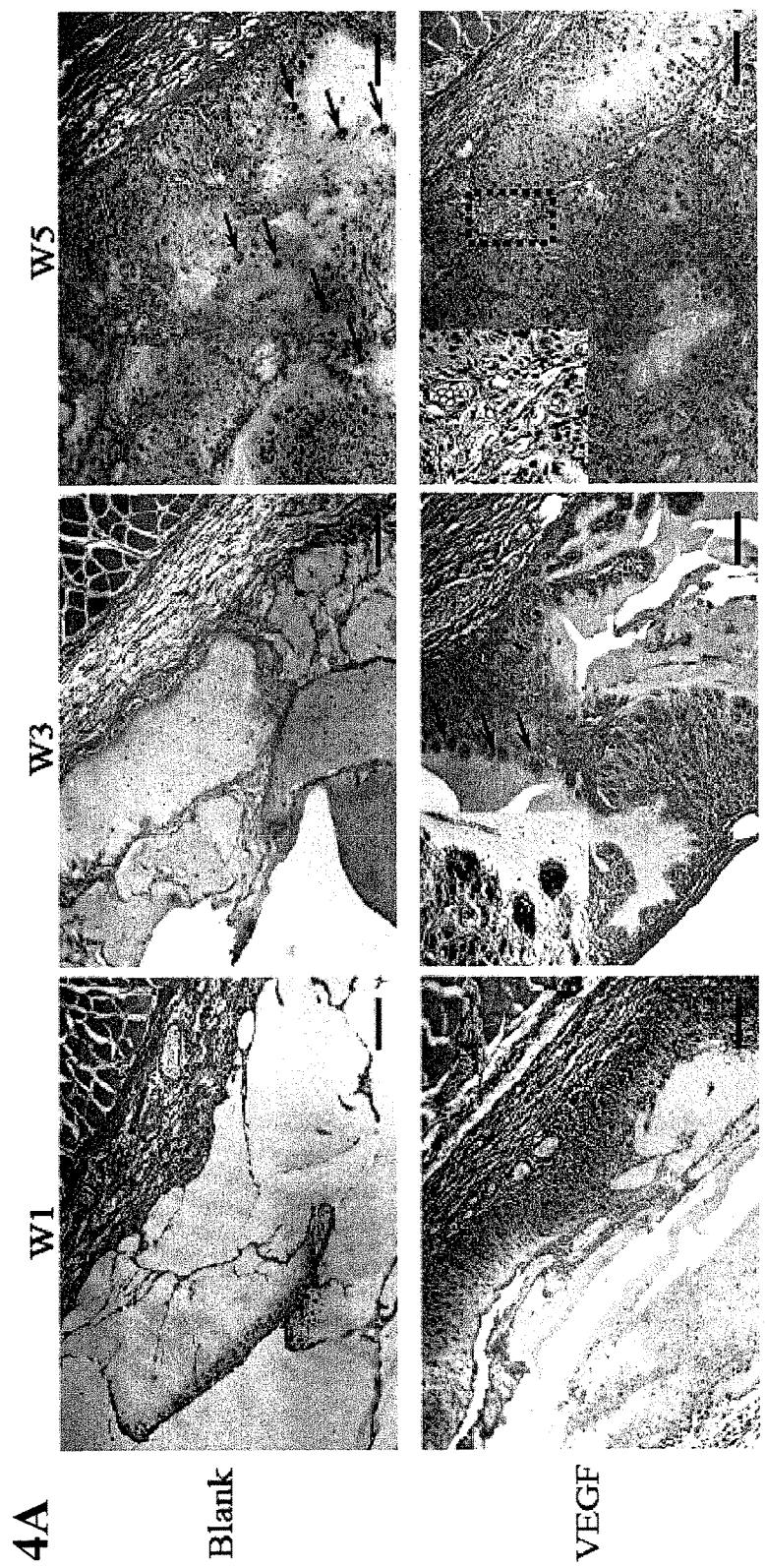
FIG. 4 shows progress of tissue ingrowth in response to VEGF delivery.
Figure 4B:
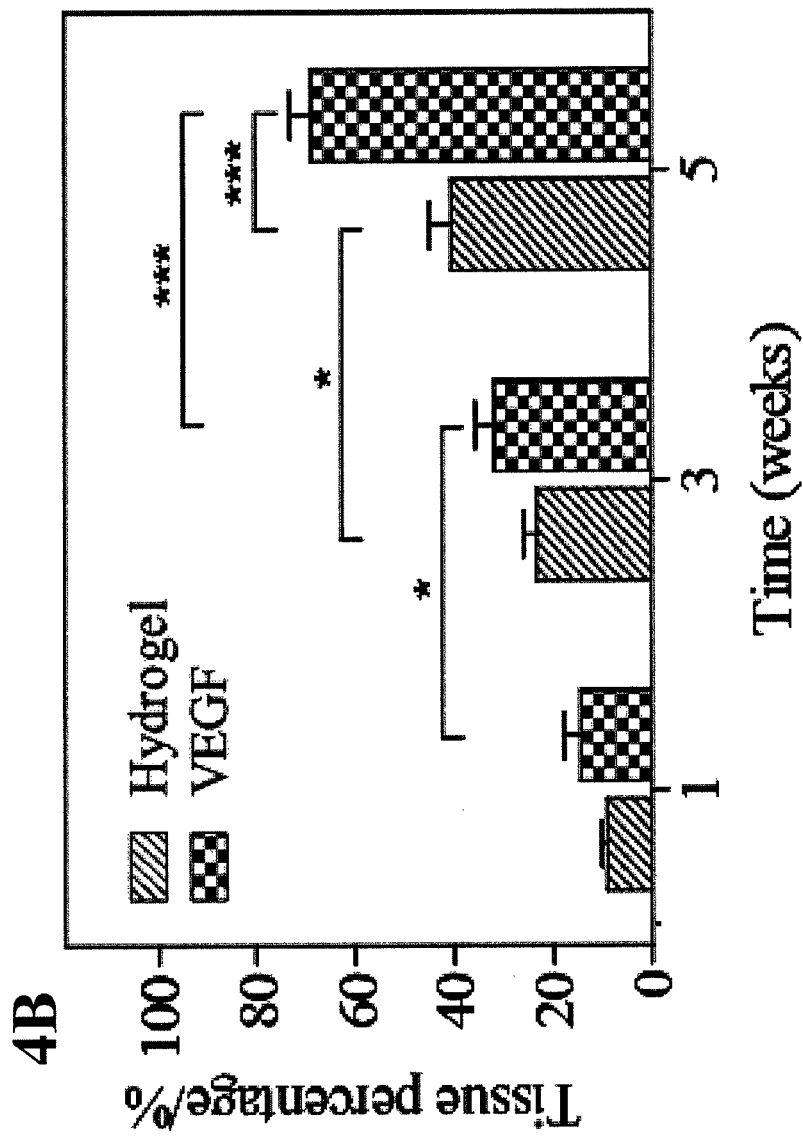
FIG. 4B shows quantification of tissue ingrowth. Significance levels were set at: *$p<0.05$, $p<0.01$, and *$p<0.001$. Values shown are means±SD. Scale bars=100 µm

VEGF was encapsulated in the hydrogel and examined tissue response and vascularization over five weeks in vivo. After one week, no significant difference in tissue ingrowth between blank hydrogel and VEGF-encapsulated hydrogel (9% and 14%, respectively; FIG. 4) was observed. After three weeks, more tissue grew into the hydrogels than during the first week; however, no significant difference was observed between the blank and VEGF-encapsulated hydrogels. After three weeks, the newly formed tissues within the blank hydrogel and the VEGF-encapsulated hydrogels occupied about 23% and 31% of the hydrogels, respectively. Compared to the tissue ingrowth after one week, significant tissue ingrowth was observed in the VEGF-encapsulated hydrogel after three weeks ($p<0.01$), suggesting that the presence of VEGF enhanced tissue ingrowth. FIG. 4A also shows that, three weeks after transplantation, multinucleated giant cells were observed in the VEGF-encapsulated hydrogel, while giant cells were observed in blank hydrogel only after five weeks; the presence of these cells demonstrates the innate response to foreign material. After five weeks, tissue ingrowth occupied more of the hydrogel, with about 40% of the blank hydrogel and 70% of the VEGF-encapsulated hydrogel overtaken by tissue ingrowth. At five weeks, both hydrogels showed significant tissue ingrowth compared to that at the end of three weeks. More importantly, the VEGF-encapsulated hydrogel had significantly greater tissue ingrowth than the blank hydrogel ($p<0.001$), further implicating the bioactive role of VEGF in promoting tissue ingrowth. Upon closer inspection at 5 weeks, vasculature containing blood cells was observed within the VEGF-encapsulated hydrogel (note dotted box in FIG. 4A).

Figure 5:
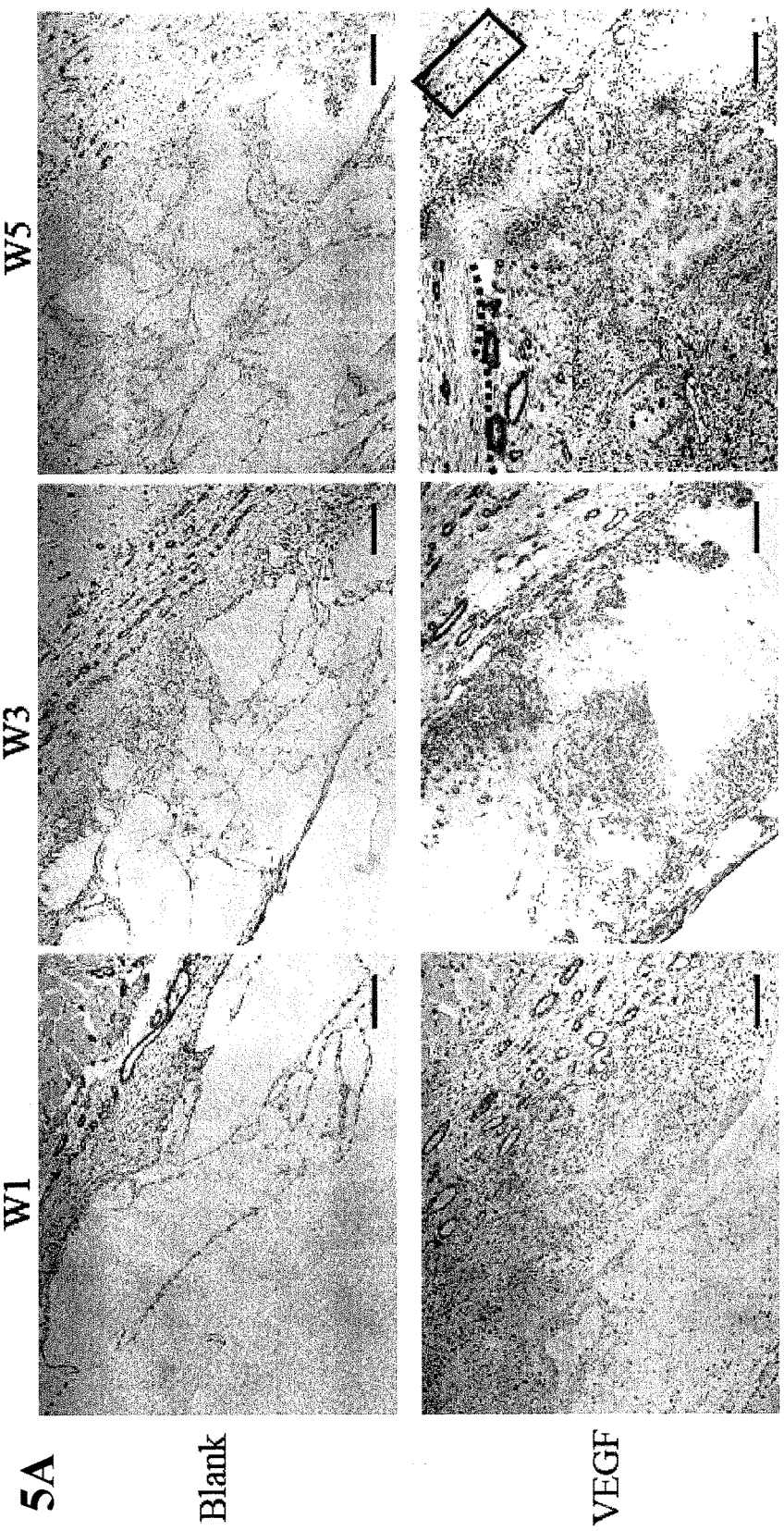
FIG. 5 shows progress of vascularization in response to VEGF delivery.

To investigate the vascularization, tissue sections were stained with anti-$\alpha$-SMA. Although no arterioles or venules were detected within the blank hydrogel over the transplantation period, distinct vascular structures were observed within the VEGF-loaded hydrogel after five weeks (FIG. 5A). Arterioles were present in the granulation layer surrounding the gel in both blank and VEGF-loaded gels but were only present in the tissue ingrowth in the VGEF-loaded hydrogels, which indicates an accelerated neovascularization process. The number of $\alpha$-SMA+ blood vessels in the granulation layer was quantified. With the encapsulation of VEGF, about 800 blood vessels/mm$^2$ formed surrounding the hydrogel during the first week, while only 280 blood vessels/mm$^2$ formed surrounding the blank hydrogel, thus clearly demonstrating that the encapsulation and release of VEGF promoted angiogenesis. The number of blood vessels surrounding the VEGF-encapsulated hydrogels decreased with time, which suggests that blood vessel density decreased as the healing proceeded. However, a significant increase in the number of blood vessels formed surrounding blank hydrogel (from 280 to approximately 600/mm$^2$) was observed after three weeks, while the number of blood vessels surrounding the blank hydrogels decreased to 410/mm$^2$ after five weeks, indicating that some blood vessels regressed as the healing proceeded. A decrease in the number of blood vessels was observed in VEGF-encapsulated hydrogels after five weeks (FIG. 5B). Analysis of the size of the arterioles and venules in the granulation layer revealed dilated blood vessels during the first week (FIG. 5C). In both VEGF-encapsulated and blank hydrogels, blood vessels became less dilated with time. For instance, the mean diameter of arterioles and venules surrounding the VEGF-encapsulated hydrogels was about 40 μm at the end of one week, and dropped to 16 μm and 10 μm within three weeks and five weeks, respectively. However, no significant difference was observed in the diameter of blood vessels between the blank hydrogel and VEGF encapsulated hydrogel. Although the number and size of blood vessels in the granulation layer diminished over five weeks, more blood vessels were found within the fragmenting VEGF-encapsulated hydrogel, which is shown by the high-magnification insert and arrows (FIG. 5A). It should be noted that the hydrogels degraded after five weeks in vivo, limiting the experiment for this transplantation period.

Figure 6:
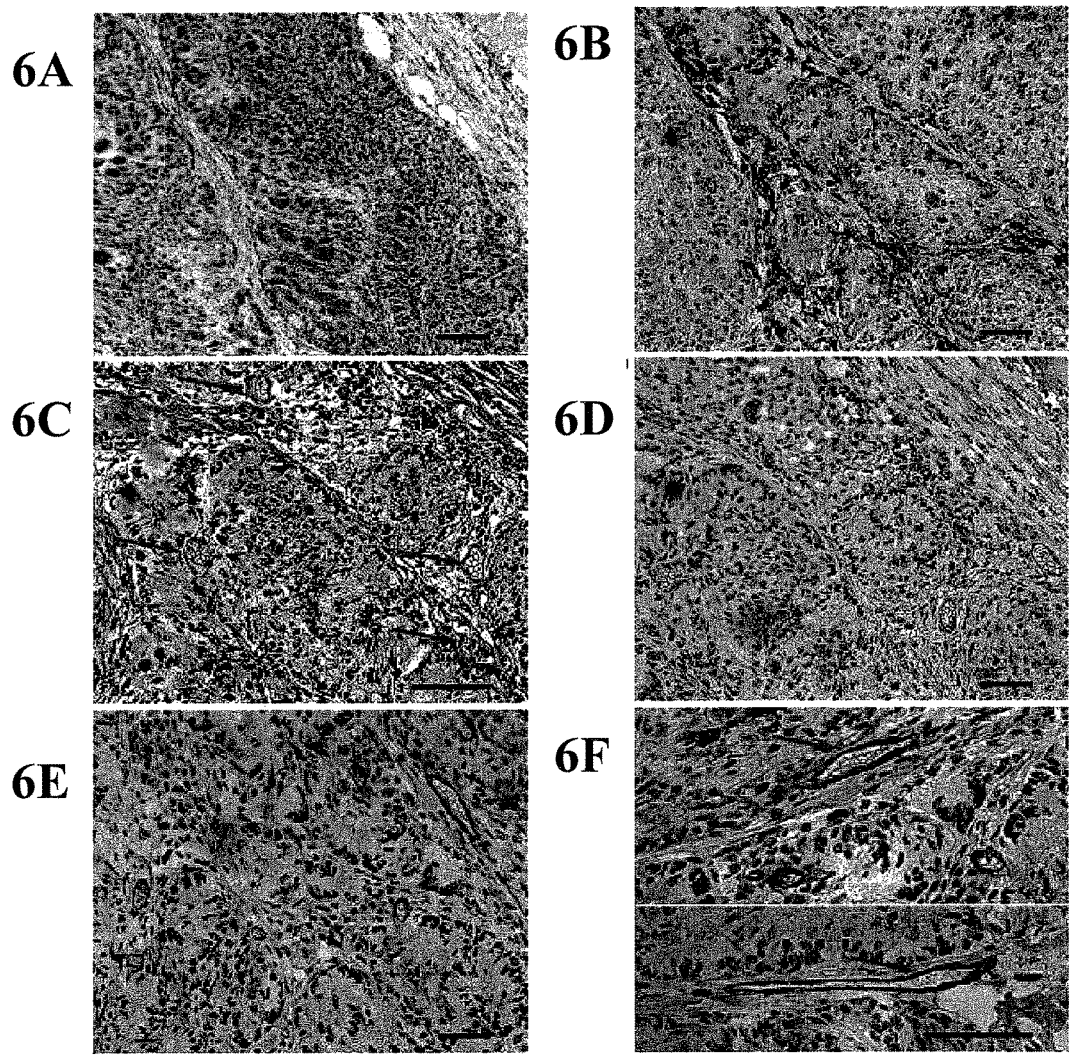
FIG. 6 shows cellular makeup in VEGF-encapsulated Dex-AE/PEGDA hydrogels after 5 weeks. Histological sections stained with anti-ED1 (FIG. 6A); CD3 (FIG. 6B); H&E (FIG. 6C); CD31 (FIG. 6D); and α-SMA (FIGS. 6E and 6F). Arrows indicate red blood cells in blood vessels within the hydrogels. Scale bars=100 µm.

To better determine the cellular make-up of the tissue ingrowth within the VEGF-loaded hydrogel after five weeks, the tissue sections with specific markers of interest were investigated. Macrophages made up much of the tissue surrounding the hydrogel (FIG. 6A), which is generally the first stage of the tissue response. Anti-CD3 staining indicated that there were T cells along the fibrovascular tracts (FIG. 6B), which is a common location for inflammatory cells. Since T cells utilize the blood vessels to enter the tissue and subsequently accumulate along them, the presence of T cells may suggest neovascularization within the hydrogel scaffold. Indeed, high-magnification examination of the H&E- (FIG. 6C), anti-CD31- (FIG. 6D), and anti-α-SMA-stained sections (FIG. 6E-F) confirmed the formation of vascular structures within the hydrogels. Meanwhile, red blood cells were observed within the larger blood vessels, indicating that the blood vessels were also functional.

Figure 7:
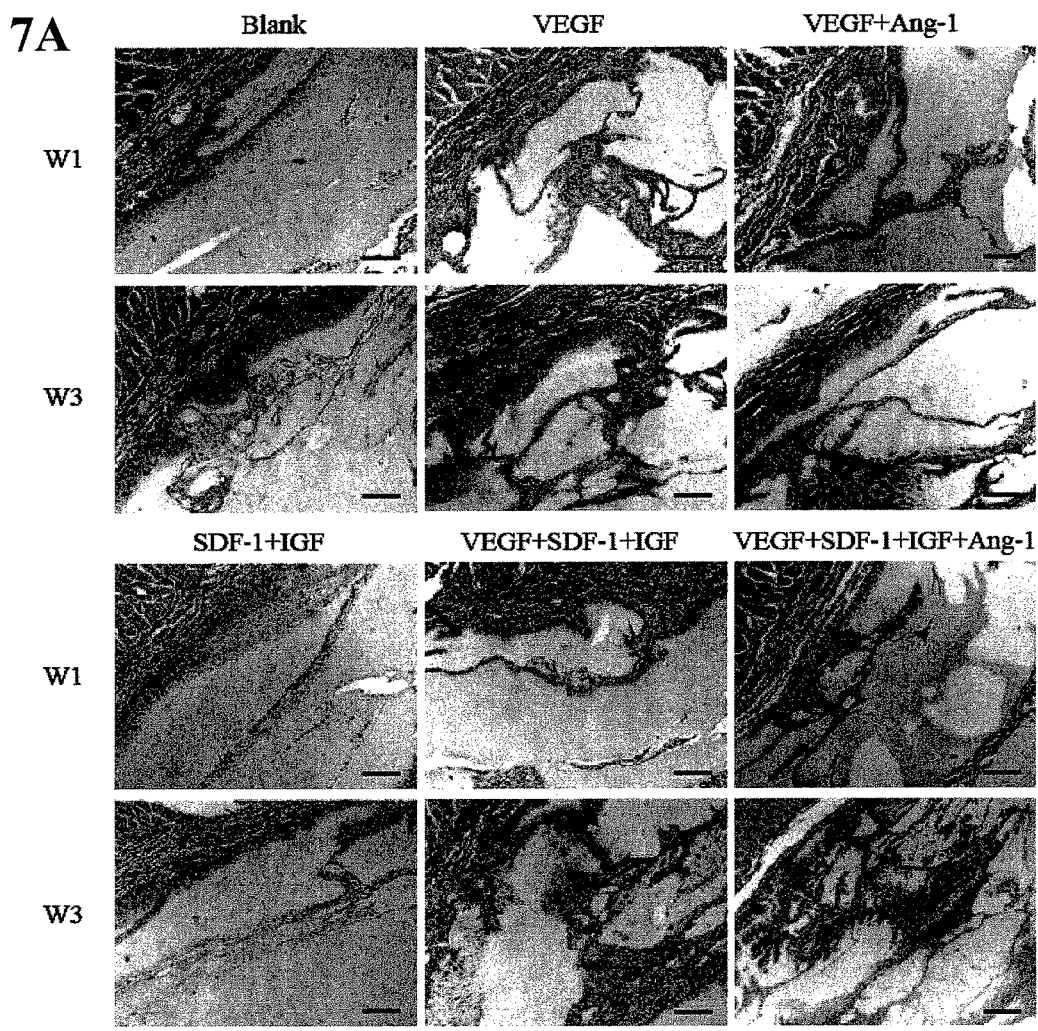
FIG. 7 shows enhanced scaffold vascularization with delivery of VEGF and other angiogenic GFs.
Figure 8:
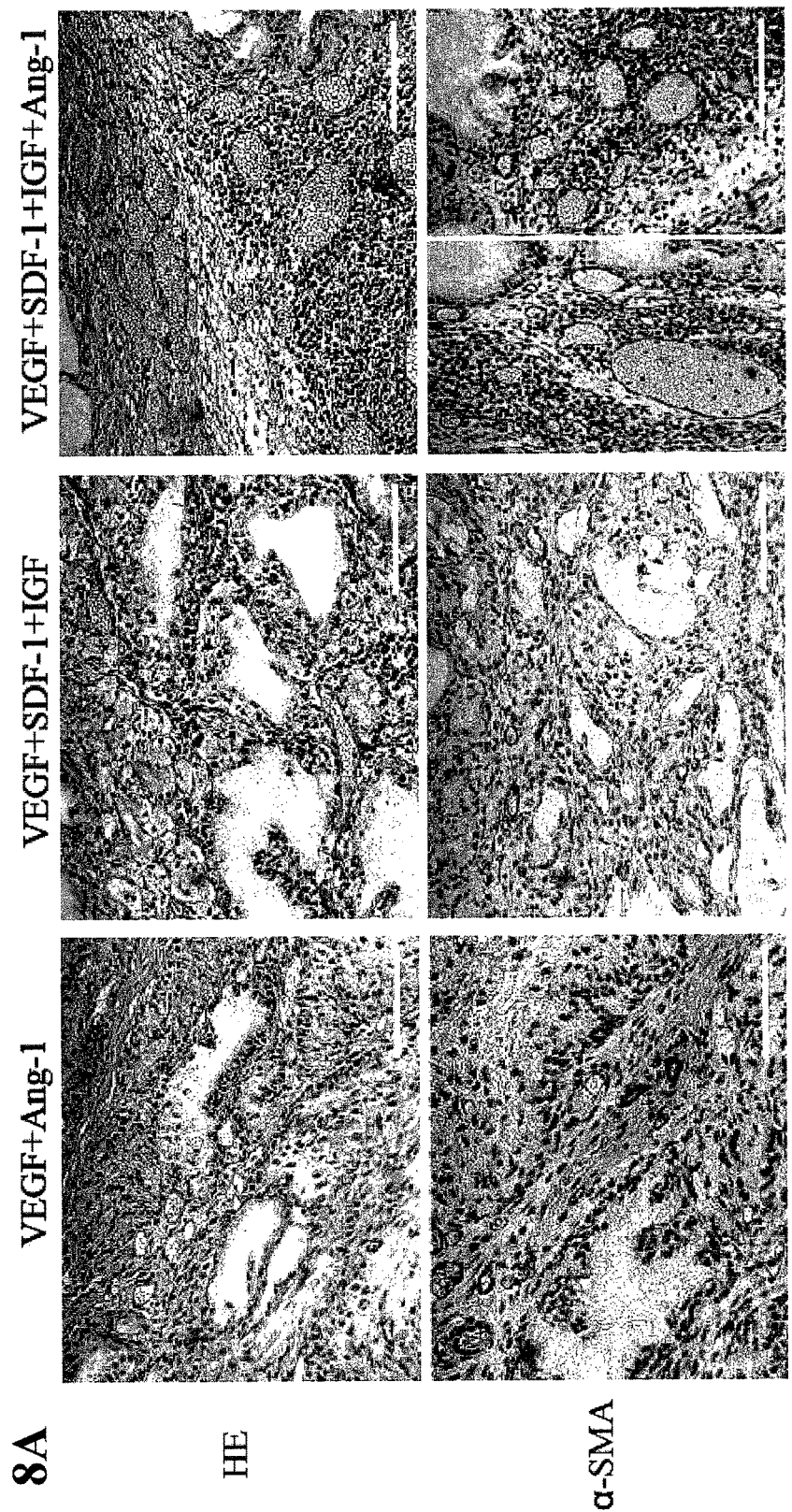
FIG. 8 shows robust scaffold vascularization with delivery of multiple GFs.
Figure 9:
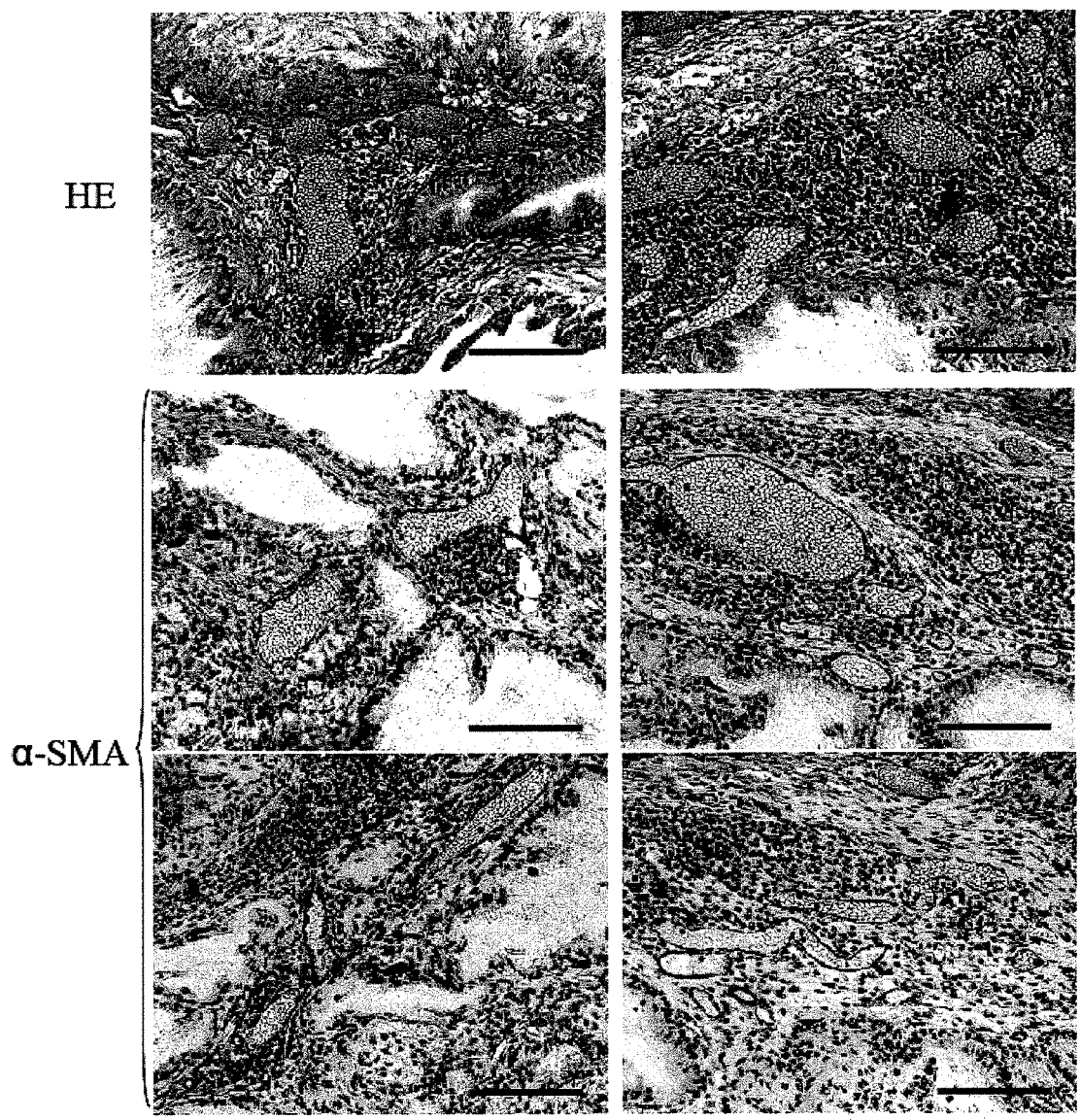
FIG. 9 shows representative images of H&E and α-SMA staining of histologic sectioning of Dex-AE/PEGDA with VEGF+SDF−1+IGF+Ang-1. Scale bars=100 µm.

Example 5—VEGF Delivery is Required for Functional Neovascularization and Synergistically Enhanced by Additional Angiogenic GFs VEGF delivery promoted healing, but vascularization within the hydrogels was observed only after five weeks. To enhance scaffold vascularization within the 80/20 hydrogels, co-encapsulation of VEGF with SDF-1, IGF and Ang-1 was investigated. Tissue ingrowth was found to vary slightly between the different hydrogels after one week of transplantation, with more pronounced differences after three weeks of transplantation (FIG. 7A). Tissue ingrowth significantly increased between one and three weeks in all hydrogels, except for the blank hydrogel and the SDF-1- and IGF-encapsulated hydrogels (FIG. 7B). Furthermore, these two hydrogels demonstrated a similar extent of tissue ingrowth, indicating that the presence of VEGF is required to enhance tissue ingrowth over the intrinsic properties of the hydrogels studied. Hydrogels loaded with combinations of GFs, which included VEGF (i.e., VEGF, SDF-1, and IGF and VEGF, SDF-1, IGF, and Ang-1) demonstrated significant tissue ingrowth after three weeks. Additionally, functional blood vessels (indicated by arrows in FIG. 7A) were observed after three weeks in hydrogels encapsulated with VEGF and Ang-1; VEGF, SDF-1, and IGF; and VEGF, SDF-1, IGF, and Ang-1. High-resolution analysis of α-SMA+ blood vessels within hydrogels encapsulated with VEGF and Ang-1; VEGF, SDF-1, and IGF; and VEGF, SDF-1, IGF, and Ang-1 clearly depict the enhanced neovascularization via arterioles and venules present in these hydrogels (FIG. 8A; FIG. 9). In contrast, hydrogels encapsulated with VEGF alone produced no detectable blood vessels present within the hydrogel (data not shown). Furthermore, delivery of all four GFs yielded significantly more and larger blood vessels (FIG. 8B-C). For example, the diameters of blood vessels induced by VEGF and Ang-1 and VEGF, SDF-1, and Ang-1 were 24 μm and 28 μm, respectively, while the delivery of VEGF, SDF-1, IGF, and Ang-1 dramatically increase diameters to 66 μm. In the meantime, the blood vessels/mm$^2$ induced by VEGF, SDF-1, IGF, and Ang-1 was about 130, significantly higher than the blood vessel numbers induced by VEGF and Ang-1 (50/mm$^2$) and VEGF, SDF-1, and Ang-1 (32/mm$^2$).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:
1. A composition comprising
vascular endothelial growth factor (VEGF);
at least one additional growth factor; and
a dextran with at least one monomer having at least one substituted hydroxyl group, wherein the substituted hydroxyl group has the formula (III); wherein formula (III) is

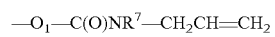

and $O_1$ is the oxygen atom of said substituted hydroxyl group and $R^7$ is hydrogen or $C_1$-$C_4$ alkyl;
wherein:
the degree of substitution of formula (III) on the dextran is from about 0.09 to less than 0.2,
the dextran is crosslinked with poly(ethylene glycol) diacrylate,
and the ratio of dextran to poly(ethylene glycol) diacrylate is about 80:20.

2. The composition of claim 1 wherein the additional growth factor is selected from the group consisting of angiopoietin, stromal cell-derived factor, insulin-like growth factor, platelet-derived growth factor, stem cell factor and combinations thereof.

3. The composition of claim 1 wherein the additional growth factor is angiopoietin.

4. The composition of claim 1 wherein the additional growth factor is a combination of stromal cell-derived factor, and insulin-like growth factor.

5. The composition of claim 1 wherein the additional growth factor is a combination of angiopoietin, stromal cell-derived factor, and insulin-like growth factor.

6. The composition of claim 1, wherein R is hydrogen.

7. The composition of claim 1, wherein the dextran further comprises a second substituted hydroxyl group having the formula (IV), where formula (III) and formula (IV) are different, and the substituted hydroxyl group of formula (III) and formula (IV) may be on the same or different monomers; wherein formula (IV) is

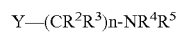

where Y is —$O_1$— or —$O_1C(O)$—, or —$O_1C(O)NR^1$—, $O_1$ is the oxygen atom of said substituted hydroxyl group, and $R^1$ is hydrogen or $C_1$-$C_4$ alkyl; n=1, 2, 3, or 4; and $R^4$ and $R^5$ are independently hydrogen or C1-C4 alkyl;

$R^2$ and $R^3$ are independently hydrogen, C1-C4 alkyl, or may combine to form a 3-6 membered ring, and when n>1, $R^2$ and $R^3$ on adjacent carbons may form a double or triple bond, or $R^2$ and $R^3$ on different carbon atoms may form a 3-6 membered ring.

8. The composition of claim 1, wherein the dextran has an average molecular weight of between about 20,000 and about 200,000.

9. The composition of claim 1, wherein the poly(ethylene glycol) diacrylate has a molecular weight of between about 2000 and about 50,000.

10. A hydrogel comprising the composition of claim 1.

11. A method of increasing neovascularization comprising administering to a subject in need thereof a composition according to claim 1.

12. The method of claim 11, wherein the administering is implanting.

13. The method of 11, wherein increasing neovascularization increases tissue regeneration, or increases healing of tissues or organs.

14. The composition of claim 3, further comprising a growth factor selected from the group consisting of stromal cell-derived factor, insulin-like growth factor, platelet-derived growth factor, stem cell factor and combinations thereof.

15. The composition of claim 1, wherein the additional growth factor is an angiogenic growth factor.

* * * * *